(12) United States Patent
Connor et al.

(10) Patent No.: US 8,315,358 B2
(45) Date of Patent: Nov. 20, 2012

(54) STRAIN MATCHING OF CRYSTALS AND HORIZONTALLY-SPACED MONOCHROMATOR AND ANALYZER CRYSTAL ARRAYS IN DIFFRACTION ENHANCED IMAGING SYSTEMS AND RELATED METHODS

(75) Inventors: Dean Connor, Shirley, NY (US); Zhong Zhong, Stony Brook, NY (US); Christopher Parham, Raleigh, NC (US); Etta Pisano, Chapel Hll, NC (US)

(73) Assignee: Nextray, Inc., Chapel Hill, NC (US)

( * ) Notice: Subject to any disclaimer, the term of this patent is extended or adjusted under 35 U.S.C. 154(b) by 232 days.

(21) Appl. No.: 12/793,228

(22) Filed: Jun. 3, 2010

(65) Prior Publication Data

US 2010/0310047 A1 Dec. 9, 2010

Related U.S. Application Data

(60) Provisional application No. 61/183,998, filed on Jun. 4, 2009, provisional application No. 61/184,004, filed on Jun. 4, 2009.

(51) Int. Cl.
G21K 1/06 (2006.01)
(52) U.S. Cl. ............................................ 378/84; 378/87
(58) Field of Classification Search .................... 378/62, 378/70–90, 98.11, 98.12
See application file for complete search history.

(56) References Cited

U.S. PATENT DOCUMENTS

| | | | |
|---|---|---|---|
| 3,598,471 A | 8/1971 | Baldwin et al. | |
| 3,639,039 A | 2/1972 | Rhodes, Jr. | |
| 3,801,785 A | 4/1974 | Barrett | |
| 3,882,310 A | 5/1975 | Barrett | |
| 3,925,660 A | 12/1975 | Albert | |
| 3,993,398 A | 11/1976 | Noguchi et al. | |
| 4,007,375 A | 2/1977 | Albert | |
| 4,284,844 A | 8/1981 | Belles | |
| 4,310,227 A | 1/1982 | Zinchuk | |
| 4,517,599 A | 5/1985 | Zwirn et al. | |

(Continued)

FOREIGN PATENT DOCUMENTS

WO    WO 02/12871 A1    2/2002

(Continued)

OTHER PUBLICATIONS

Ex Parte Quayle Action dated Apr. 6, 2012 for related U.S. Appl. No. 12/708,579, filed Feb. 19, 2012.

(Continued)

Primary Examiner — Courtney Thomas
(74) Attorney, Agent, or Firm — Olive Law Group, PLLC

(57) ABSTRACT

Strain matching of crystals and horizontally-spaced monochromator and analyzer crystal arrays in diffraction enhanced imaging systems and related methods are disclosed. A DEI system, including strain matched crystals can comprise an X-ray source configured to generate a first X-ray beam. A first monochromator crystal can be positioned to intercept the first X-ray beam for producing a second X-ray beam. A second monochromator crystal can be positioned to intercept the second X-ray beam to produce a third X-ray beam for transmission through an object. The second monochromator crystal has a thickness selected such that a mechanical strain on a side of the first monochromator crystal is the same as a mechanical strain on the second monochromator crystal. An analyzer crystal has a thickness selected such that a mechanical strain on a side of the first monochromator crystal is the same as a mechanical strain on the analyzer crystal.

105 Claims, 20 Drawing Sheets

U.S. PATENT DOCUMENTS

| | | |
|---|---|---|
| 4,532,548 A | 7/1985 | Zwirn |
| 4,647,154 A | 3/1987 | Birnbach et al. |
| 4,718,075 A | 1/1988 | Horn |
| 4,882,619 A | 11/1989 | Hasegawa et al. |
| 5,008,908 A | 4/1991 | Jach et al. |
| 5,123,036 A | 6/1992 | Uno et al. |
| 5,127,028 A | 6/1992 | Wittry |
| 5,164,975 A | 11/1992 | Steinmeyer |
| 5,195,115 A | 3/1993 | Schiller et al. |
| 5,237,598 A | 8/1993 | Albert |
| 5,245,648 A | 9/1993 | Kinney et al. |
| 5,259,013 A | 11/1993 | Kuriyama et al. |
| 5,319,694 A | 6/1994 | Ingal et al. |
| 5,339,305 A | 8/1994 | Curtis et al. |
| 5,347,400 A | 9/1994 | Hunter |
| 5,406,609 A | 4/1995 | Arai et al. |
| 5,428,657 A | 6/1995 | Papanicolopoulos et al. |
| 5,430,807 A | 7/1995 | Gravely |
| 5,457,726 A | 10/1995 | Miyazaki |
| 5,457,727 A | 10/1995 | Frijlink |
| 5,532,814 A | 7/1996 | Cha |
| 5,535,291 A | 7/1996 | Spencer et al. |
| 5,541,026 A | 7/1996 | Matsumoto |
| 5,579,363 A | 11/1996 | Ingal et al. |
| 5,596,620 A | 1/1997 | Canistraro et al. |
| 5,634,669 A | 6/1997 | Colgate, Jr. |
| 5,635,720 A | 6/1997 | Mooney et al. |
| 5,667,736 A | 9/1997 | Chien |
| 5,682,412 A | 10/1997 | Skillicorn et al. |
| 5,715,291 A | 2/1998 | Momose |
| 5,717,733 A | 2/1998 | Kurbatov et al. |
| 5,787,146 A | 7/1998 | Giebeler |
| 5,801,889 A | 9/1998 | Meyers et al. |
| 5,802,137 A | 9/1998 | Wilkins |
| 5,805,342 A | 9/1998 | Gravely |
| 5,805,662 A | 9/1998 | Kurbatov et al. |
| 5,835,561 A | 11/1998 | Moorman et al. |
| 5,850,425 A | 12/1998 | Wilkins |
| 5,867,264 A | 2/1999 | Hinnrichs |
| 5,923,720 A | 7/1999 | Barton et al. |
| 5,933,277 A | 8/1999 | Troxell et al. |
| 5,949,847 A | 9/1999 | Terada et al. |
| 5,953,161 A | 9/1999 | Troxell et al. |
| 5,969,864 A | 10/1999 | Chen et al. |
| 5,974,211 A | 10/1999 | Slater |
| 5,987,095 A | 11/1999 | Chapman et al. |
| 6,038,285 A | 3/2000 | Zhong et al. |
| 6,041,098 A | 3/2000 | Touryanski et al. |
| 6,086,708 A | 7/2000 | Colgate, Jr. |
| 6,088,425 A | 7/2000 | Ono |
| 6,100,978 A | 8/2000 | Naulleau et al. |
| 6,163,593 A | 12/2000 | Koller et al. |
| 6,221,579 B1 | 4/2001 | Everhart et al. |
| 6,226,349 B1 | 5/2001 | Schuster et al. |
| 6,269,144 B1 | 7/2001 | Dube et al. |
| 6,320,648 B1 | 11/2001 | Brueck et al. |
| 6,349,004 B1 | 2/2002 | Fischer et al. |
| 6,353,656 B1 | 3/2002 | LeVert et al. |
| 6,385,289 B1 | 5/2002 | Kikuchi |
| 6,399,295 B1 | 6/2002 | Kaylor et al. |
| 6,411,367 B1 | 6/2002 | Baker et al. |
| 6,517,490 B1 | 2/2003 | Garlick |
| 6,525,806 B1 | 2/2003 | Smith |
| 6,573,040 B2 | 6/2003 | Everhart et al. |
| 6,577,708 B2 * | 6/2003 | Chapman et al. ............... 378/82 |
| 6,685,641 B2 | 2/2004 | Liu |
| 6,754,307 B2 | 6/2004 | Brendler et al. |
| 6,757,104 B2 | 6/2004 | Nakai |
| 6,760,399 B2 | 7/2004 | Malamud |
| 6,804,324 B2 | 10/2004 | Martynov et al. |
| 6,836,530 B2 | 12/2004 | Singer et al. |
| 6,870,896 B2 | 3/2005 | Protopopov |
| 6,927,748 B2 | 8/2005 | Hughes et al. |
| 6,947,521 B2 | 9/2005 | Wernick et al. |
| 6,953,643 B2 | 10/2005 | Bourdillon |
| 6,980,378 B2 | 12/2005 | Lee |
| 6,987,616 B2 | 1/2006 | Tamada et al. |
| 6,991,895 B1 | 1/2006 | Yen et al. |
| 7,012,989 B2 | 3/2006 | Holland et al. |
| 7,062,015 B2 | 6/2006 | Lewis |
| 7,076,025 B2 | 7/2006 | Hasnah et al. |
| 7,095,510 B2 | 8/2006 | Fukui |
| 7,120,228 B2 | 10/2006 | Yokhin et al. |
| 7,183,547 B2 | 2/2007 | Yun et al. |
| 7,193,767 B1 | 3/2007 | Peeri |
| 7,224,528 B2 | 5/2007 | Phillips et al. |
| 7,242,744 B2 | 7/2007 | Brauss |
| 7,245,696 B2 | 7/2007 | Yun et al. |
| 7,330,530 B2 | 2/2008 | Chapman |
| 7,352,845 B2 | 4/2008 | Uda |
| 7,409,041 B2 | 8/2008 | Grassmann et al. |
| 7,421,060 B2 | 9/2008 | Zienert et al. |
| 7,431,464 B2 | 10/2008 | Park |
| 7,443,952 B2 | 10/2008 | Dosho et al. |
| 7,471,766 B2 | 12/2008 | Dosho |
| 7,535,992 B2 | 5/2009 | Taguchi et al. |
| 7,542,547 B2 | 6/2009 | Kogan |
| 7,564,947 B2 | 7/2009 | Cernik |
| 7,646,849 B2 | 1/2010 | Iwasaki et al. |
| 7,711,088 B2 | 5/2010 | Gibson et al. |
| 7,724,871 B2 | 5/2010 | Boyden et al. |
| 7,742,563 B2 | 6/2010 | Edic et al. |
| 7,742,564 B2 | 6/2010 | Parham et al. |
| 2003/0112421 A1 | 6/2003 | Smith |
| 2003/0149357 A1 | 8/2003 | Liu |
| 2004/0101676 A1 | 5/2004 | Phillips et al. |
| 2004/0121241 A1 | 6/2004 | Kodama |
| 2004/0196957 A1 | 10/2004 | Ando |
| 2005/0062928 A1 | 3/2005 | Yau et al. |
| 2005/0069696 A1 | 3/2005 | King et al. |
| 2005/0269818 A1 | 12/2005 | Forde |
| 2006/0039532 A1 | 2/2006 | Wu et al. |
| 2007/0013983 A1 | 1/2007 | Kitamura et al. |
| 2007/0024828 A1 | 2/2007 | Liao et al. |
| 2007/0291896 A1 | 12/2007 | Parham et al. |

FOREIGN PATENT DOCUMENTS

| | | |
|---|---|---|
| WO | WO 2007/087328 A2 | 8/2008 |
| WO | 2010065532 A2 | 6/2010 |
| WO | WO 2010/065532 A2 | 6/2010 |
| WO | WO 2010/141734 A2 | 12/2010 |
| WO | WO 2010/141735 A2 | 12/2010 |
| WO | 2010037276 | 12/2011 |

OTHER PUBLICATIONS

Applicant's Amendment dated Apr. 9, 2012 for related U.S. Appl. No. 12/708,579, filed Feb. 19, 2012.

Notice of Allowance dated May 11, 2012 for related U.S. Appl. No. 12/708,579, filed Feb. 19, 2012.

Notification of Transmittal of the International Search Report and the Written Opinion of the International Searching Authority, or the Declaration for related PCT International Application No. PCT/US2010/037276 to NEXTRAY, Inc.

Notification of Transmittal of International Preliminary Examination Report for PCT International Application No. PCT/US07/01836 to the University of North Carolina at Chapel Hill.

Written Opinion of the International Searching Authority for PCT International Application No. PCT/US07/01836 to the University of North Carolina at Chapel Hill.

Patent Application No. 2007/80009742.9 has been published in the Chinese Patent Gazette on Apr. 8, 2009 as Publication No. CN 101405596 A.

Indian Patent Application No. 4155/CHENP/2008 has been published in the Patent Office Journal on Mar. 13, 2009.

Related U.S. Appl. No. 12/708,579 to Dean Connor.

Keyrilainen J et al., Refraction contrast in X-ray imaging, Nuclear Instruments & Method in Physics Research, Section A, vol. 488, No. 1-2, Aug. 1, 2002, pp. 419-427.

Annex to Form PCT/ISA/206 dated Aug. 14, 2012 for corresponding Int'l. Application PCT/US20101037277; includes partial search.

* cited by examiner

STRAIN MATCHING OF CRYSTALS AND HORIZONTALLY-SPACED MONOCHROMATOR AND ANALYZER CRYSTAL ARRAYS IN DIFFRACTION ENHANCED IMAGING SYSTEMS AND RELATED METHODS

CROSS REFERENCE TO RELATED APPLICATIONS

This application claims the benefit of U.S. provisional patent application No. 61/183,998, filed Jun. 4, 2009, and U.S. provisional patent application No. 61/184,004, filed Jun. 4, 2009, the contents of which are incorporated herein in their entireties.

TECHNICAL FIELD

The subject matter disclosed herein relates to X-ray imaging. More particularly, the subject matter disclosed herein relates to strain matching crystals and horizontally-spaced monochromator and analyzer crystal arrays in diffraction enhanced imaging systems and related methods.

BACKGROUND

X-ray imaging has been used in a variety of fields for imaging objects. For example, X-ray imaging has been used extensively in the medical field for non-destructive testing and X-ray computed tomography (CT). Various other types of technology are also being used for medical imaging. For example, diffraction enhanced imaging (DEI) is an X-ray imaging technique that dramatically extends the capability of conventional X-ray imaging.

The DEI technique is an X-ray imaging modality capable of generating contrast from X-ray absorption, X-ray refraction, and ultra-small angle scatter rejection (extinction). In contrast, conventional X-ray imaging techniques measure only X-ray attenuation. The DEI absorption image and peak image shows the same information as a conventional radiograph, except that it is virtually free of scatter degradation. Based on Bragg's law of X-ray diffraction, $n\lambda=2d\sin(\theta)$, DEI utilizes the Bragg peak of perfect crystal diffraction to convert angular changes into intensity changes, providing a large change in intensity for a small change in angle. Thus, DEI is well suited to soft-tissue imaging, and very promising for mammography.

The use of a silicon analyzer crystal in the path of the X-ray beam generates two additional forms of image contrast, X-ray refraction, and extinction (ultra small angle scatter rejection). DEI utilizes highly collimated X-rays prepared by X-ray diffraction from perfect single-crystal silicon. These collimated X-rays are of single X-ray energy, practically monochromatic, and are used as the beam to image an object.

Objects that have very little absorption contrast may have considerable refraction and extinction contrast, thus improving visualization and extending the utility of X-ray imaging. Applications of DEI techniques to biology and materials science have generated significant gains in both contrast and resolution, indicating the potential for use in mainstream medical imaging. An area of medicine where DEI may be particularly effective is in breast imaging for cancer diagnosis, where the diagnostic structures of interest often have low absorption contrast, making them difficult to see. Structures with low absorption contrast, such as the spiculations extending from a malignant mass, have high refraction and ultra-small angle scatter contrast. It is desirable to provide a DEI system with the capability to increase both the sensitivity and specificity of X-ray-based breast imaging.

Multiple studies have demonstrated improved image contrast in both medical and industrial applications of DEI. Advantages of DEI systems over conventional X-ray imaging systems in the medical field include a dramatic reduction in patient radiation dose and improved image quality. The dose reduction is due to the ability of DEI systems to function at higher X-ray energies. X-ray absorption is governed by the photoelectric effect, $Z^2/E^3$, where Z is the atomic number and E is the photon energy.

The core theory of DEI is based on Bragg's law of X-ray diffraction. Bragg's law is defined by the following equation:

$$n\lambda=2d\sin(\theta)$$

where $\lambda$ is the wavelength of the incident X-ray beam, $\theta$ is the angle of incidence, d is the distance between the atomic layers in the crystal, and n is an integer.

A monoenergetic radiograph contains several components that can affect image contrast and resolution: a coherently scattered component $I_C$, an incoherently scattered component $I_I$, and a transmitted component. X-rays passing through an object or medium where there are variations in density can be refracted, resulting in an angular deviation. Specifically, deviations in the X-ray range result from variations in pt along the path of the beam, where $\rho$ is the density and t is the thickness. A fraction of the incident photons may also be diffracted by structures within an object, which are generally on the order of milliradians and referred to as small angle scattering. The sum total of these interactions contributed to the recorded intensity in a radiograph $I_N$, which can be represented by the following equation:

$$I_N=I_R+I_D+I_C+I_I$$

System spatial resolution and contrast will be degraded by the contributions of both coherent and incoherent scatter. Anti-scatter grids are often used in medical imaging to reduce the contribution of scatter, but their performance is limited and use of a grid often requires a higher dose to compensate for the loss in intensity.

The DEI technique utilizes a silicon analyzer crystal in the path of the post-object X-ray beam to virtually eliminate the effects of both coherent and incoherent scatter. The narrow angular acceptance window of the silicon analyzer crystal is referred to as its rocking curve, and is on the order of microradians for the X-ray energies used in DEI. The analyzer acts as an exquisitely sensitive angular filter, which can be used to measure both refraction and extinction contrast. Extinction contrast is defined as the loss of intensity from the incident beam due to scattering, which can produce substantial improvements in both contrast and resolution.

The Darwin Width (DW) is used to describe reflectivity curves, and is approximately the Full Width at Half Maximum (FWHM) of the reflectivity curve. Points at $-\frac{1}{2}$ DW and $+\frac{1}{2}$ DW are points on the curve with a steep slope, producing the greatest change in photon intensity per microradian for a particular analyzer reflection and beam energy. Contrast at the peak of the analyzer crystal rocking curve is dominated by X-ray absorption and extinction, resulting in near scatter-free radiographs. Refraction contrast is highest where the slope of the rocking curve is greatest, at the $-\frac{1}{2}$ and $+\frac{1}{2}$ DW positions. One DEI based image processing technique uses these points to extract the contrast components of refraction and apparent absorption from these image pairs.

The following paragraph describes this technique for extracting the contrast components of refraction and apparent absorption from an image pair. When the analyzer crystal is set to an angle representing +/−½ DW for a given reflection and beam energy, the slope of the rocking curve is relatively consistent and can be represented as a two-term Taylor series approximation as represented by the following equation:

$$R(\theta_0 + \Delta\theta_Z) = R(\theta_0) + \frac{dR}{d\theta}(\theta_0)\Delta\theta_Z.$$

If the analyzer crystal is set to the low-angle side of the rocking curve (−½ DW), the resulting image intensity can be represented by the following equation:

$$I_L = I_R\left(R(\theta_L) + \frac{dR}{d\theta}\bigg|_{\theta=\theta_L} \Delta\theta_Z\right).$$

The recorded intensity for images acquired with the analyzer crystal set to the high-angle position (+½ DW) can be represented by the following equation:

$$I_H = I_R\left(R(\theta_H) + \frac{dR}{d\theta}(\theta_H)\Delta\theta_Z\right).$$

These equations can be solved for the changes in intensity due to apparent absorption ($I_R$) and the refraction in angle observed in the z direction ($\Delta\theta_Z$) represented by the following equation:

$$\Delta\theta_Z = \frac{I_H R(\theta_L) - I_L R(\theta_H)}{I_L\left(\frac{dR}{d\theta}\right)(\theta_H) - I_H\left(\frac{dR}{d\theta}\right)(\theta_L)}$$

$$I_R = \frac{I_L\left(\frac{dR}{d\theta}\right)(\theta_H) - I_H\left(\frac{dR}{d\theta}\right)(\theta_L)}{R(\theta_L)\left(\frac{dR}{d\theta}\right)(\theta_H) - R(\theta_H)\left(\frac{dR}{d\theta}\right)(\theta_L)}.$$

These equations can be applied to the high and low angle images on a pixel-by-pixel basis to separate the two contrast elements into what is known as a DEI apparent absorption and refraction image. However, it is important to note that each of the single point rocking curve images used to generate DEI apparent absorption and refraction images is useful.

Development of a clinical DEI imager may have significance for women's health and medical imaging in general for the following reasons: (1) DEI has been shown to produce very high contrast for the features that are most important to detection and characterization of breast cancer; (2) the physics of DEI allows for imaging at higher x-ray energies than used with absorption alone; and (3) the ability of DEI to generate contrast without the need of photons to be absorbed dramatically reduces ionization, and thus reduces the absorbed dose.

Further, screen-film mammography has been studied extensively for the last 40 years, and because of many large randomized screening trials, it is known to reduce breast cancer mortality by approximately 18-30%. The rate of breast cancer death in the last few years has begun to decline, likely due in part to the widespread use of this imaging test. However, standard screen-film mammography is neither perfectly sensitive nor highly specific. Dense breast tissue and diffuse involvement of the breast with tumor tends to reduce the sensitivity of screening mammography. For women with dense breasts, lesions that develop are difficult to see because their ability to absorb photons is not much greater than the surrounding adipose tissue, generating little contrast for visualization. Approximately 10-20% of breast cancers that are detected by self-examination or physical examination are not visible by screen-film mammography. In addition, when lesions are detected by mammography and biopsy, only 5-40% of lesions prove to be malignant. Furthermore, approximately 30% of breast cancers are visible in retrospect on prior mammograms.

Current DEI and DEI imaging processing techniques are based heavily on conventional imaging theory and rely, at least in part, on X-ray absorption for image generation. Thus, objects imaged using these techniques absorb radiation. Such radiation exposure is undesirable in applications for medical imaging given concerns of dose, and this reasoning places considerable engineering limitations that make clinical and industrial translation challenging. Thus, it is desirable to provide DEI and DEI techniques that produce high quality images and that rely less on absorption but produce images with equivalent diagnostic quality and feature visualization.

Accordingly, in light of desired improvements associated with DEI and DEI systems, there exists a need for improved DEI and DEI systems and related methods for detecting an image of an object.

SUMMARY

Strain matching of crystals and horizontally-spaced monochromator and analyzer crystal arrays in DEI systems and related methods are disclosed. For example, a DEI system, including strain matched crystals can comprise an X-ray source configured to generate a first X-ray beam. A first monochromator crystal can be positioned to intercept the first X-ray beam for producing a second X-ray beam. A second monochromator crystal can be positioned to intercept the second X-ray beam to produce a third X-ray beam for transmission through an object. The second monochromator crystal has a thickness selected such that a mechanical strain at and near the face of the first monochromator crystal is the same as a mechanical strain at and near the face of the second monochromator crystal. An analyzer crystal has a thickness selected such that a mechanical strain at and near the face of the first monochromator crystal is the same as a mechanical strain on the analyzer crystal. The analyzer crystal is positioned to intercept transmitted X-ray beams at angles of incidence of the analyzer crystal. An image detector can be configured to detect an image of the object from a beam diffracted from the analyzer crystal.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

Figure 1:
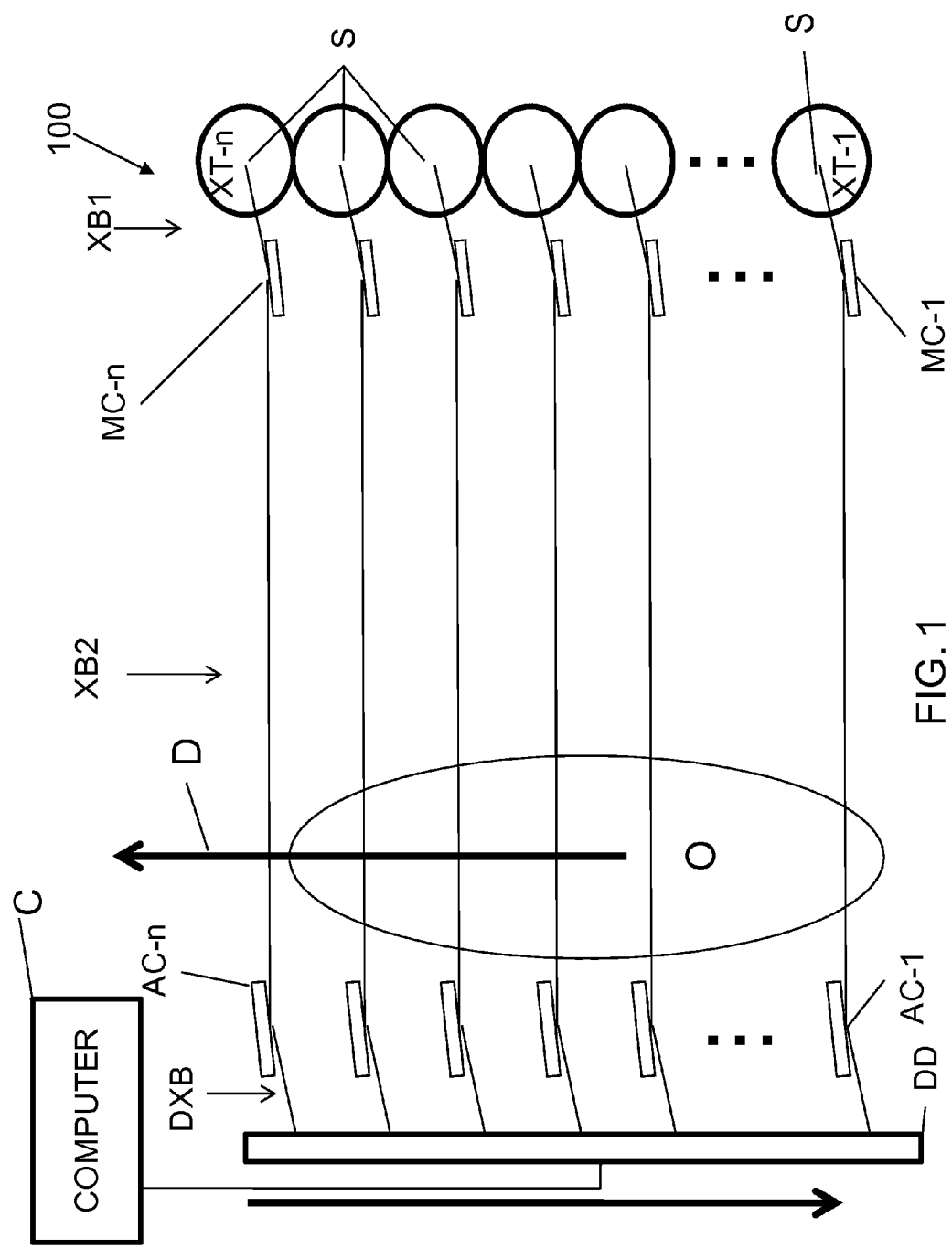
FIGS. 1-11 are schematic diagrams of different example DEI systems including multiple monochromator crystals and multiple small area sources according to embodiments of the subject matter described herein.

The subject matter of the presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

The subject matter described herein discloses strain matching of crystals in DEI systems. According to one aspect, the subject matter described herein can include a DEI system can comprise an X-ray source configured to generate a first X-ray beam. A first monochromator crystal can be positioned to intercept the first X-ray beam for producing a second X-ray beam. A second monochromator crystal can be positioned to intercept the second X-ray beam to produce a third X-ray beam for transmission through an object. The second monochromator crystal has a thickness and width selected such that a mechanical strain on a side of the first monochromator crystal is the same as a mechanical strain on the second monochromator crystal. An analyzer crystal has a thickness and width selected such that a mechanical strain on a side of the first monochromator crystal is the same as a mechanical strain on the analyzer crystal. The analyzer crystal is positioned to intercept transmitted X-ray beams at angles of incidence of the analyzer crystal. An image detector can be configured to detect an image of the object from a beam diffracted from the analyzer crystal.

An image processing technique using DEI in accordance with the subject matter described herein can use images acquired at symmetric points of the rocking curve to generate apparent absorption and refraction images of an object. A DEI apparent absorption image is similar to a conventional radiograph image, but exhibits much greater contrast owing to scatter rejection. DEI refraction images can depict the magnitude of small beam deflections caused by large-scale refractive-index features (features of a size at or greater than the system resolution). A DEI extinction image is generated at points on the rocking curve where the primary mechanism of contrast is due to photons that have been scattered by an object on the order of microradians. Another DEI based imaging processing technique is referred to as Multiple Image Radiography (MIR) which uses multiple points on the rocking curve to generate quantitative images representing an object's X-ray absorption, refraction, and ultra-small angle scatter. Systems and methods in accordance with the subject matter described herein can generate images at any point on the analyzer rocking curve, and can thus be used to generate: (1) single image DEI at any analyzer position; (2) DEI apparent absorption and refraction images; and (3) mass density images. The ability to generate the raw image data required for these processes and any other DEI based processing technique are useful for all DEI based processing techniques. In addition, systems and methods described herein are amenable for use in computed tomography, and can provide the raw data for use in any DEI-based computed tomography algorithm.

As understood, a small area source may refer to any source capable of generating X-ray beams from a small area in space. For example, an X-ray tube may include multiple small area sources for emitting X-ray beams from multiple points. The small area sources may be within the same X-ray tube source. Alternatively or in addition to being a part of a system as disclosed herein, multiple X-ray tube sources may each provide one or more small area sources and be used together for generating multiple X-ray beams.

The subject matter disclosed herein provides an additional advantage of providing spacing between individual DEI crystal optics arrays and improved heat dissipation with the source anode due the power load being delivered to several, separated points, both advancements over a single-source, multiple-beam design. This applies to one beam per small area source (wherein the number of beams equals the number of small area sources) as well as multiple beams per source point (if each source generates n beams, then the beams will number n times the number of small area sources).

The subject matter disclosed herein is advantageous over previous DEI systems and methods, because it allows for greater mechanical separation between the individual optical elements, thereby solving the problem of potential mechanical interference between monochromator crystals. By using multiple small area sources as described herein, rather than having a single, very high power source location, the power load can be divided amongst several source locations, thus the heat load to the anode may be distributed over a larger area, which can allow for longer operating times for the tube sources. By spacing out the small area sources, the monochromator crystal sizes, as well as the size of the electromechanical control systems, can be larger as compared to previous systems. In addition, the subject matter disclosed herein can allow for greater distribution of the heating load to the anode for decreasing time between imaging sessions.

A DEI system according to one embodiment of the subject matter described herein can include multiple monochromator crystals for rejecting particular X-rays emitted by multiple X-ray small area sources. FIGS. 1-11 are schematic diagrams of different example DEI systems including multiple monochromator crystals and multiple small area sources according to embodiments of the subject matter described herein. The DEI systems are operable to produce images of an object by use of the X-ray beams generated by the multiple small area sources. The DEI systems can include multiple small area sources operable to produce a polychromatic X-ray beam, generally designated XB1. X-ray beams XB1 can include photons having different energies. In one example, the X-ray beams are generated by one or more tungsten X-ray tubes having a small area source from which an X-ray beam is emitted. In another example, a system may include multiple X-ray tube sources that each provide one or more small area sources and may be used together for generating multiple X-ray beams.

Figure 12:
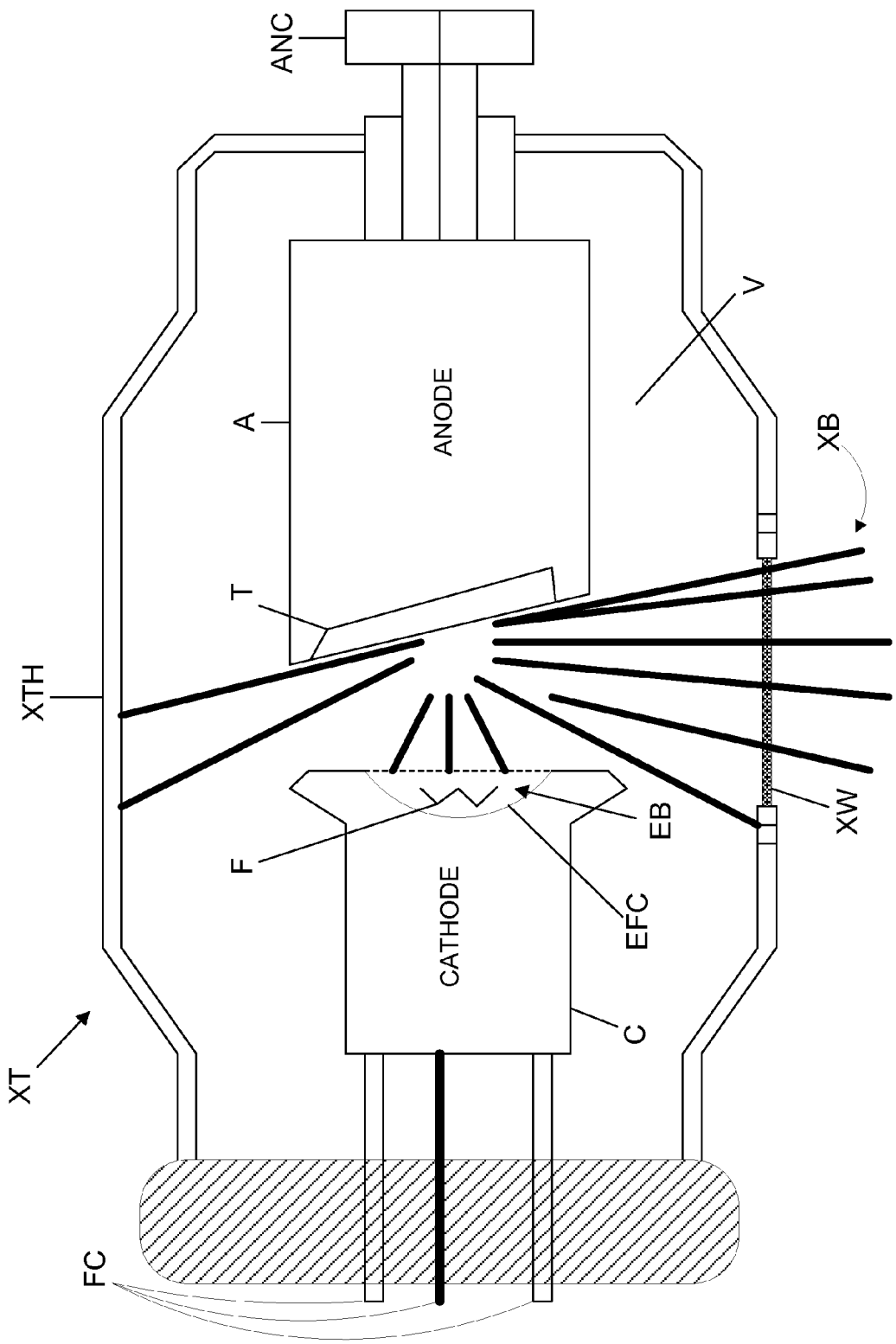
FIG. 12 is a schematic diagram of X-ray tube XT based on a stationary X-ray tube design according to an embodiment of the subject matter described herein.

FIG. 12 is a schematic diagram of X-ray tube XT based on a stationary X-ray tube design according to an embodiment of the subject matter described herein. Referring to FIG. 12, X-ray tube XT includes a cathode C configured to generate an electron beam, generally designated EB. Cathode C is made of tungsten or a tungsten alloy. A high voltage is applied across cathode C and anode A, which creates a high potential difference across a vacuum interior V of X-ray tube XT. A voltage potential can be applied to anode A via an anode connection ANC. X-ray tube XT can include a filament F configured to heat cathode C. Filament F can be connected to a power supply by filament connections FC.

Vacuum interior V is defined within X-ray tube housing XTH. Electrons may be thermonically ejected from cathode C by heating cathode C. An electrostatic focusing cup EFC surrounds the point of electron ejection, which helps to focus the electron stream towards anode A. Further, electrons being emitted from cathode C are focused across vacuum interior V to anode A, with the velocity across the gap being determined by the voltage applied across the circuit.

Electrons ejected from cathode C can be directed towards and incident upon a tungsten target T of anode A. As a result of the impact of electrons upon target T, X-ray beam XB is generated. X-ray beam XB exits vacuum interior V via an X-ray window XW. X-ray beam XB can include characteristic emission lines and Bremsstrahlung radiation.

One example of an X-ray generator is the ISOVOLT TITAN 160 available from GE Inspection Technologies of Ahrensburg, Germany. Other exemplary X-ray tubes include the COMET MXR-160 Series of X-ray tubes, such as the MXR-160HP/20 X-ray tube, which are available from Comet AG of Flamatt, Switzerland. Other exemplary X-ray tubes can include those that use anodes including tungsten, molybdenum, iron, or copper. Other suitable types of targets include a barium hexaboride target and a samarium target. A barium hexaboride target can produce X-rays at about 30 keV. Samarium's $K\alpha1$ line is at about 40 keV. In one example, an anode of an x-ray tube can be a rotating anode from which x-ray beams can be emitted. In another example, an anode of an x-ray tube can be a stationary anode from which x-ray beams can be emitted.

Referring again to FIG. 1, a DEI system, generally designated 100, includes a number N X-ray tubes XT-1-XT-N, each including at least one small area source S, for generating multiple X-ray beams XB1. An array of collimators (not shown) may be positioned adjacent each small area source S for blocking a portion of each of X-ray beams XB1 that fall outside an angular acceptance window of respective monochromator crystals MC-1-MC-n. System 100 can also include other collimators positioned between small area sources S and monochromator crystals MC-1-MC-n for blocking a portion of X-ray beams XB1 that falls outside an angular acceptance window of the monochromator crystals MC-1-MC-n. The collimators can define a slit or hole through which a portion of X-ray beams XB1 can pass to monochromator crystals MC-1-MC-n. Further, the collimators can be made of any suitable material for blocking X-ray beams such as lead.

The monochromator crystals MC-1-MC-n can be configured to select a predetermined energy of a portion of X-ray beams XB1 incident thereon. In one example, a monochromator crystal is a silicon [333] monochromator crystal adapted to reject the majority of photons of its respective X-ray beams that do not have a desired energy. For the case of a tungsten X-ray tube, there can be a range of beam energies that are reflected by the silicon monochromator crystal. In this case, the characteristic emission lines of the X-ray beams are 59.13 keV ($K\alpha1$) and 57.983 ($K\alpha2$), and the bremsstrahlung radiation that falls within the narrow angular acceptance window of the monochromator crystal. The brightness of the bremsstrahlung radiation is several orders of magnitude less than the two $K\alpha$ emission lines.

An X-ray beam may be scattered by its respective monochromator crystal in several different directions. Another array of collimators (not shown) may be positioned between the monochromator crystals MC-1-MC-n and the object O for blocking a portion of the X-ray beam that falls outside an angular acceptance window of its corresponding analyzer crystal, one of analyzer crystals AC-1-AC-n. Each collimator can define a slit or hole through which a portion of one of the X-ray beams can pass towards its analyzer crystal for interception by the analyzer crystal.

The analyzer crystals AC-1-AC-n can be rotated for measuring the amount of radiation traveling in a particular direction. The angular reflectivity function of the crystal system is called the intrinsic rocking curve, and this property is used to generate image refraction contrast. If an X-ray photon is deviated towards the peak of the rocking curve, its reflectivity, and thus intensity will increase. If an object feature causes a photon to be deflected down the rocking curve, or away from the peak reflectivity position, it will cause a reduction in intensity.

A sample or object O can be imaged in air or immersed in a coupling medium, such as water. The use of a coupling medium can be used to reduce the index gradient between the air and the object O to be imaged, thus allowing the incident X-rays to pass into the object without experiencing significant refraction at the air-object interface. This is not necessary for most objects, but it is an application of the DEI method and can be used to improve the internal contrast of an object.

In one example, a monochromator crystal is a symmetric crystal which is narrow in one dimension. A symmetric crystal's lattice planes (the atomic layers that contribute to diffracting the X-ray beam) are parallel to the surface of the crystal. A symmetric crystal preserves the vertical height of the corresponding X-ray source in the incoming beam. In comparison, an asymmetric crystal modifies the divergence and size of the incoming beam. In this example of a monochromator crystal being a symmetric crystal, two-dimensional imaging of large imaging fields (e.g., imaging fields of about 25 cm by 20 cm) can be achieved by scanning a sample object and a detector using a symmetric crystal. One exemplary advantage of a symmetric crystal over an asymmetric crystal is that the asymmetric crystal requires a large monochromator crystal to prepare the imaging beam (e.g., selecting and collimating X-rays), imposing a severe limitation on the perfection of the large crystal. Further, the size of an asymmetric crystal increases with increasing X-ray beam energy, thus making it impractical for X-rays of about 59.13 keV. In contrast, for example, a symmetric monochromator crystal used in accordance with the subject matter described herein can utilize 59.13 keV X-rays with a modest sized crystal of about 30 mm in length. An advantage, over single-beam DEI, of the system and methods disclosed herein, with multiple sources, is that this scan range can be greatly reduced, because of much better spatial coverage of the beams (i.e. if you have a required 25 cm scan range, and 10 beams, then the object will only have to be scanned through a range of 2.5 cm).

Referring again to FIG. 1, the object O can be positioned in the path of X-ray beams XB2 (the X-ray beams resulting for the interaction of X-ray beams XB1 with the monochromator crystals MC-1-MC-n) by, for example, a scanning stage (not shown) for imaging of the object O. The object O can be scanned in a direction D, which is approximately perpendicular to the direction of X-ray beams XB2. During scanning of the object O, X-ray beams XB2 can pass through object O and can be analyzed by analyzer crystals AC-1-AC-n, which can be silicon crystals that match monochromator crystals MC-1-MC-n. X-ray beams XB2 incident on analyzer crystals AC-1-AC-n can each diffract (resulting in diffraction X-ray beams, generally designated DXB) for interception by a digital detector (or image plate) DD. Digital detector DD can detect the diffracted X-ray beams DXB and generate electrical signals representative of the intercepted X-ray beams DXB.

The electrical signals can be communicated to a computer C for image analysis and display to an operator. The computer C can be configured to generate an absorption image, an image showing refraction effects, and an image depicting ultra-small-angle scattering, the types of which are described in more detail below.

The monochromator crystals can propagate their respective x-ray beams as a horizontally-divergent (FIG. 4) and partially vertically divergent (see FIG. 3) fan beam. The fan beam can be collimated with one or more collimators to shield against undesired X-rays, resulting in clear DEI images and low subject dose. In contrast to a two-dimensional beam, a fan beam can be more readily controlled for the shielding of undesired X-rays.

Figure 2:
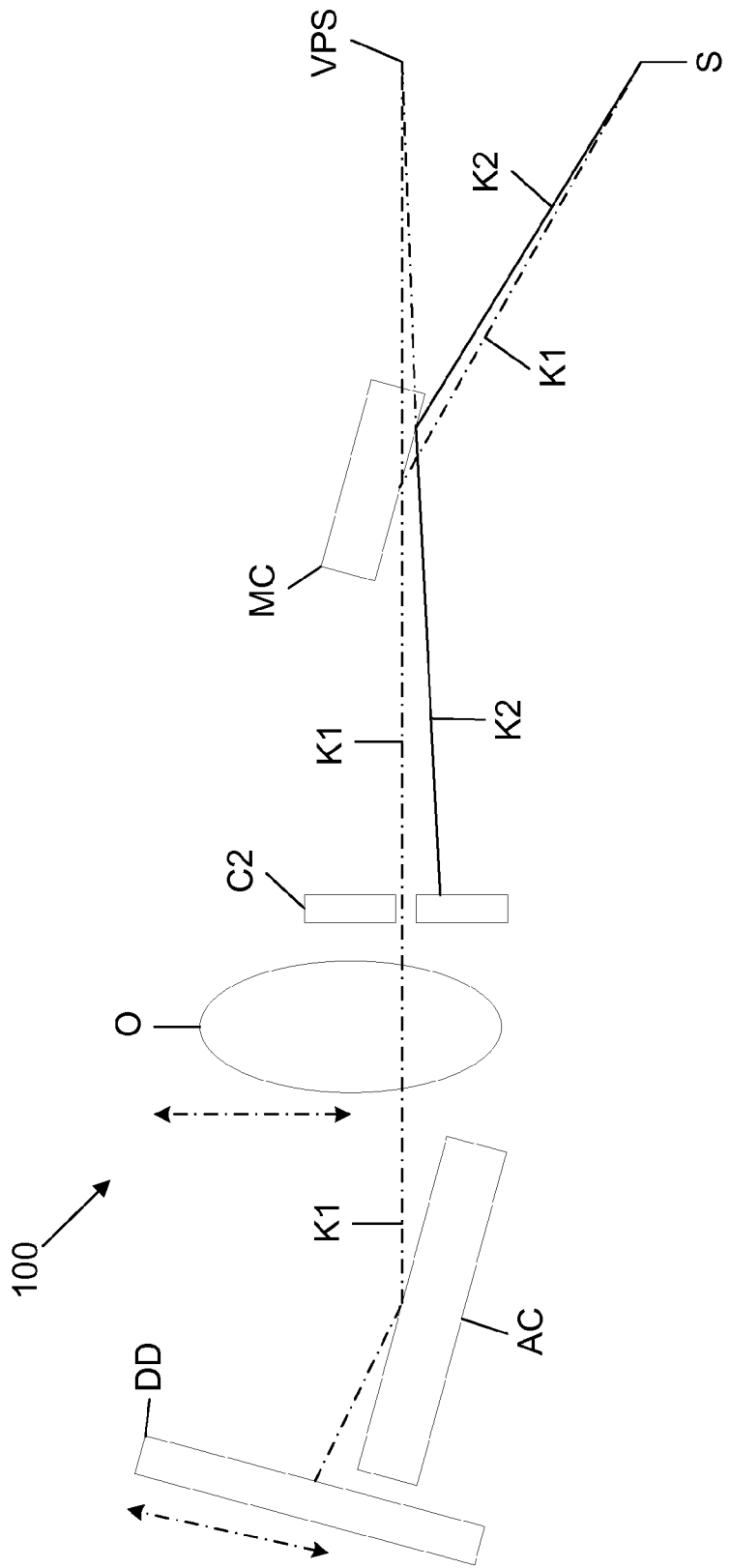
Figure 3:
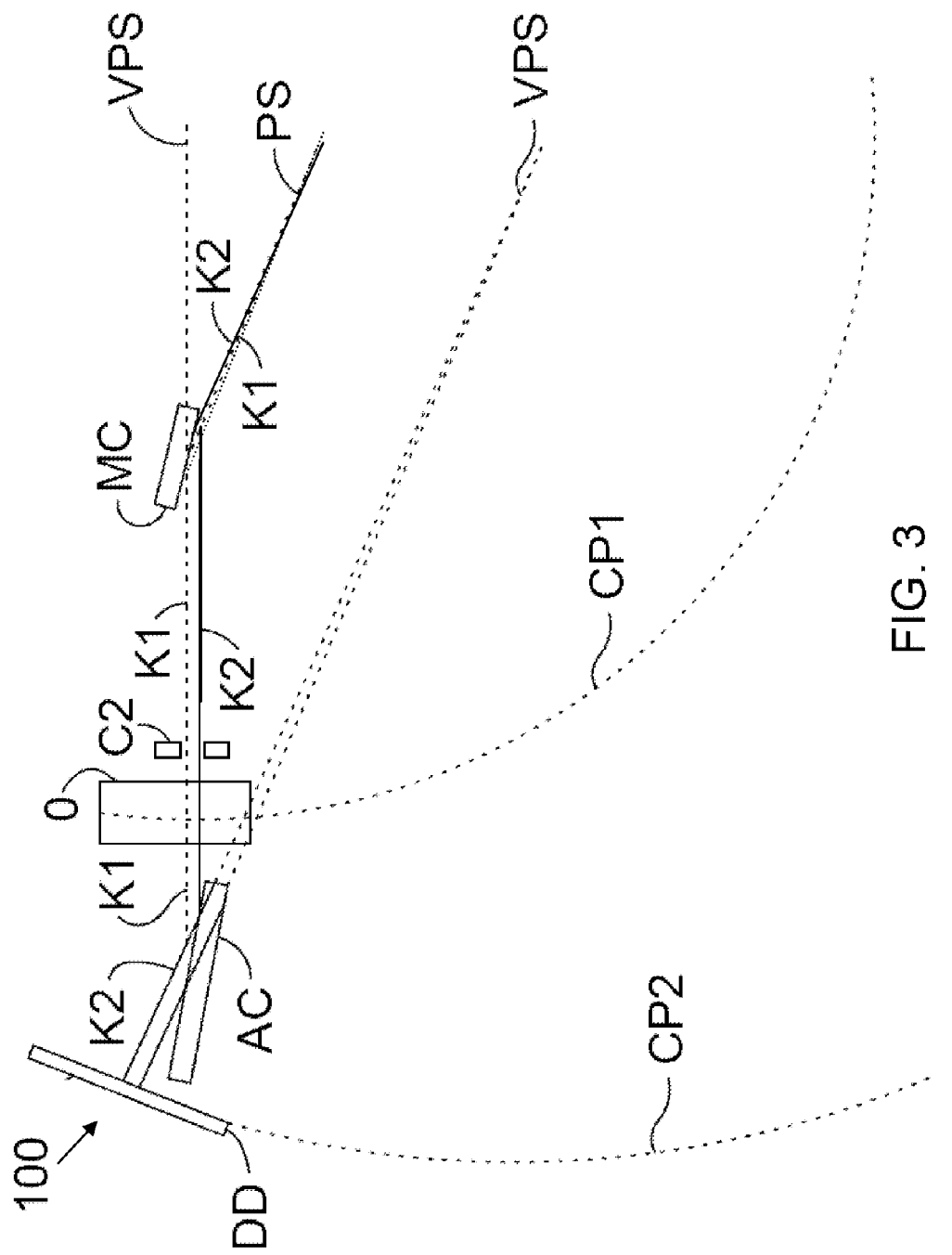

Referring now to FIGS. 2 and 3, the DEI system 100 is shown in different operation modes. For clarity, the X-ray beam generated by only one small area source S is shown. Characteristic emission lines $K\alpha1$ K1 and $K\alpha2$ K2 of the X-ray beam are generated by small area source S. Emission lines $K\alpha1$ K1 and $K\alpha2$ K2 originate from the same small area source S. As stated above, monochromator crystal MC rejects the majority of photons of the X-ray beam that do not have the desired energy. In this case, emission lines $K\alpha1$ K1 and $K\alpha2$ K2 and bremsstrahlung radiation pass monochromator crystal MC and are redirected towards an analyzer crystal AC as shown.

Collimator C2 is positioned in a path of emission lines $K\alpha1$ K1 and $K\alpha2$ K2. Collimator C2 defines an adjustable slit through which emission lines can be selectively passed towards analyzer crystal AC. In the first operational mode shown in FIG. 2, the slit is adjusted for an aperture of the vertical size of the X-ray source at a distance of about 400 mm from the small area source S, and positioned such that emission line $K\alpha1$ K1 passes collimator C2 and $K\alpha2$ K2 is blocked. Thus, collimator C2 removes all X-rays except for the X-rays from emission line $K\alpha1$ K1 and a very narrow range of bremsstrahlung radiation. In this mode, the beam is not vertically divergent and thus the object O and detector DD are scanned at the same scanning speed, in opposite directions. This mode yields a maximum possible out-of-plane resolution (the direction of DEI's contrast), but at the cost of removing a portion of the X-rays from the X-ray beam, thereby necessitating increased exposure time. The virtual small area source for the object O is designated VPS.

Referring now to FIG. 3, in the second operational mode, emission lines $K\alpha1$ K1 and $K\alpha2$ K2 and the bremsstrahlung radiation at nearby energies are passed through the collimator C2. The slit of collimator C2 is adjusted for an aperture of about 2.0 mm at a distance of about 400 mm from the small area source S and positioned such that emission lines $K\alpha1$ K1 and $K\alpha2$ K2 and the bremsstrahlung radiation passes collimator C2. In this mode, the beam divergence is taken into account. In order to avoid image blurring, the object O and detector DD can be scanned at the same angular speed. The relative scanning speeds of detector DD and the sample stage on which the object O is placed can be determined by the source-to-object distance and the source-to-detector distance (where the distances are taken along the beam path). The beam divergence in this mode can lead to lower resolution out-of-plane, but this mode has the advantage of passing more X-rays and thus allows for a faster exposure time. The virtual small area source for detector DD is designated VPS. Circle portions CP1 and CP2 are centered at the virtual source points for the object O and detector DD, respectively.

Further, in one embodiment of using the second mode, the Bremsstrahlung radiation at x-ray energies that are different from the K alpha lines can be captured. Thus, in this embodiment, the system is tunable in x-ray energy and is not limited to the characteristic emission energies. This functionality can be achieved by changing the incident angle of the monochromator crystal and the analyzer crystal. In one example, this functionality can be achieved by changing the incident angle to 11.4 degrees, following the Bragg's law, and replacing the Copper filter with an Aluminum filter. In this example, imaging can occur at 30 keV x-ray energy. X-ray energies lower than the Tungsten emission line energies can be utilized for relatively thin objects.

In one example, the copper filter can be configured to remove about 19 keV bremsstrahlung radiation for reducing or eliminating unwanted crystal reflections and harmonics. Images have the potential to be degraded without this filtering.

Figure 4:
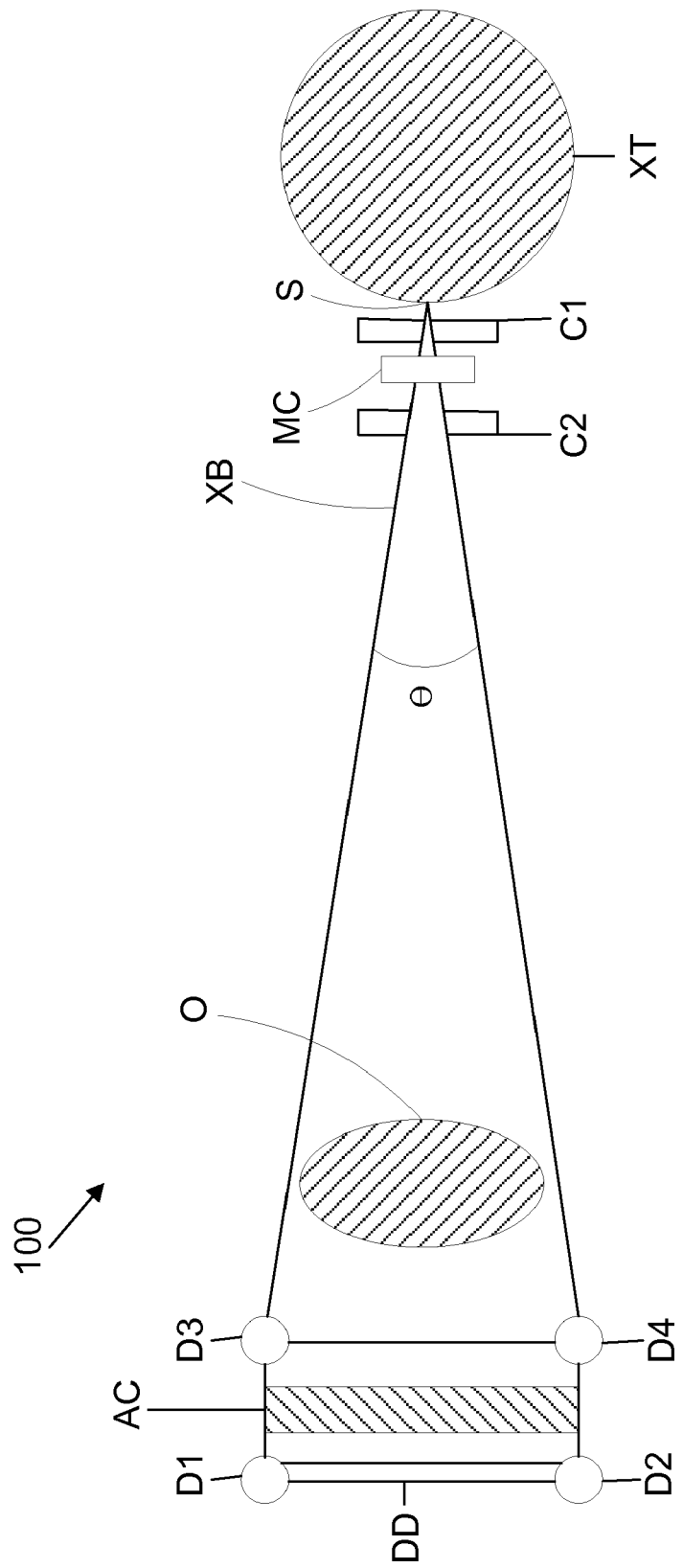

FIG. 4 is a top schematic view illustrating the DEI system 100 of FIG. 1 according to an embodiment of the subject matter described herein. For clarity, the X-ray beam XB generated by only one small area source S of an X-ray tube is shown. Referring to FIG. 4, X-ray beam XB are generated by a source of X-ray tube XT. Collimators C1 and C2 block the horizontal spread of the portion of X-ray beam XB to define the angular spread of the X-ray beam XB and its horizontal size at the object O position. The portion of X-ray beam XB that passes through collimators C1 and C2 is the X-ray beam portion that passes through slits in the collimators. The angle θ may be about 17° or any other suitable angle.

The DEI system 100 can include right and left post-analyzer crystal sodium iodide detectors D1 and D2, respectively, and right and left post-monochromator crystal sodium iodide detectors D3 and D4, respectively. Detectors D3 and D4 are used to ensure alignment of the monochromator crystals (MC) and detectors D1 and D2 are used to ensure analyzer crystal (AC) alignment. These detectors are used to measure the intensity of the diffracted X-ray beam being emitted from the monochromator crystal MC, or the analyzer AC. For system alignment, detectors D1 and D2 are placed in the post analyzer crystal AC X-ray beam XB. If the analyzer crystal is not tuned to the desired angle, the intensity measured by the detectors D1 and D2 will show this and the system can be adjusted. The same is true for the detectors in the post-monochromator crystal MC X-ray beam XB. In addition, detectors D1-D4 can be used to measure X-ray beam XB in real time and adjust the analyzer crystal, D1 and D2, chi (angle as measured about the axis along the X-ray beam path) or monochromator crystal chi, D3 and D4. The use of these detectors to set, measure, and adjust the analyzer crystal AC and monochromator crystal MC can be important for successful DEI image acquisition.

Figure 5:
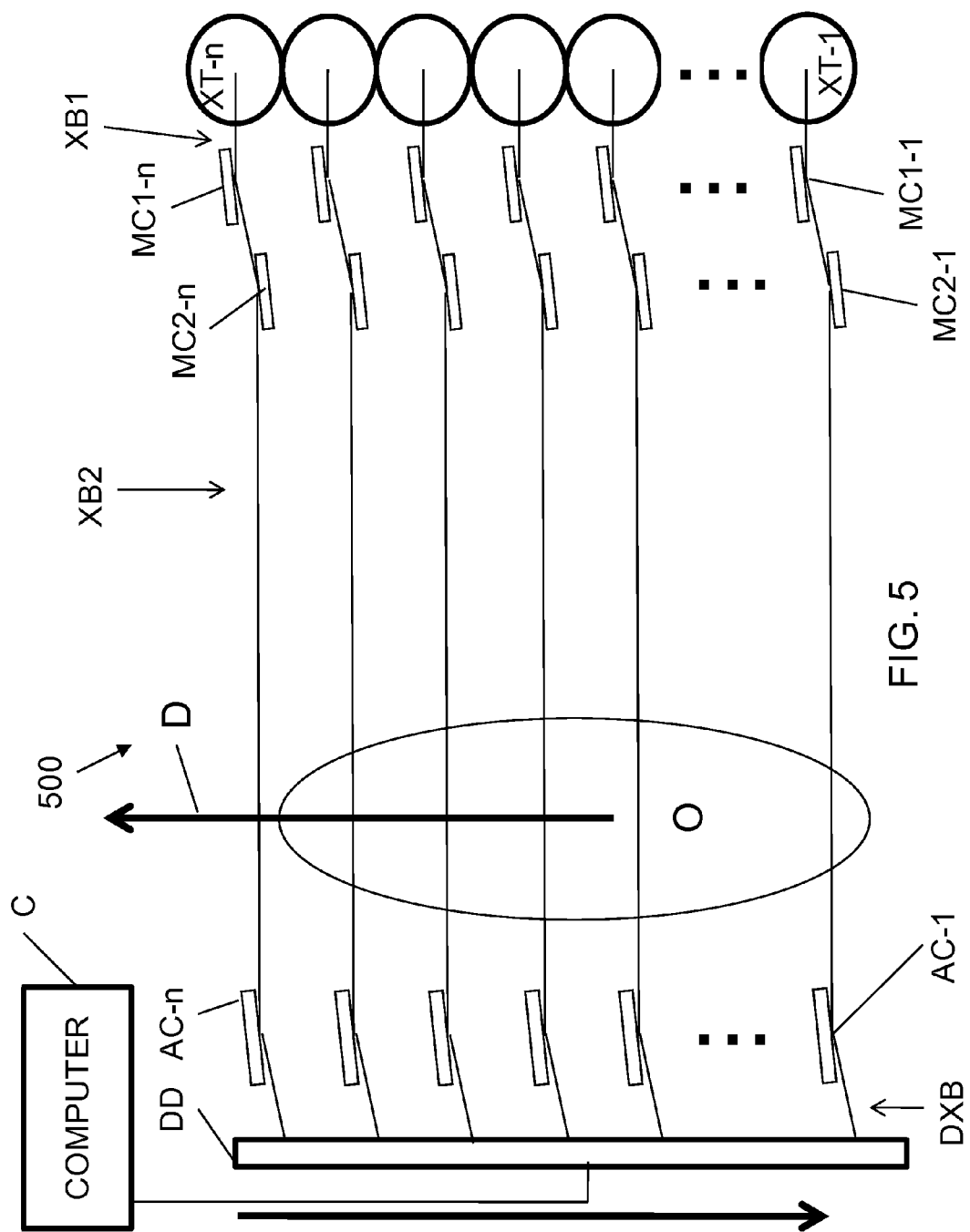

Referring now to FIG. 5, another example DEI system 500 for detecting an image of the object O according to an embodiment of the subject matter disclosed herein is shown. The DEI system 500 is similar to DEI system 100 shown in FIG. 1 except that DEI system 500 includes a second set of monochromator crystals MC2-1-MC2-n positioned downstream from a first set of monochromator crystals MC1-1-MC1-n.

Figure 6:
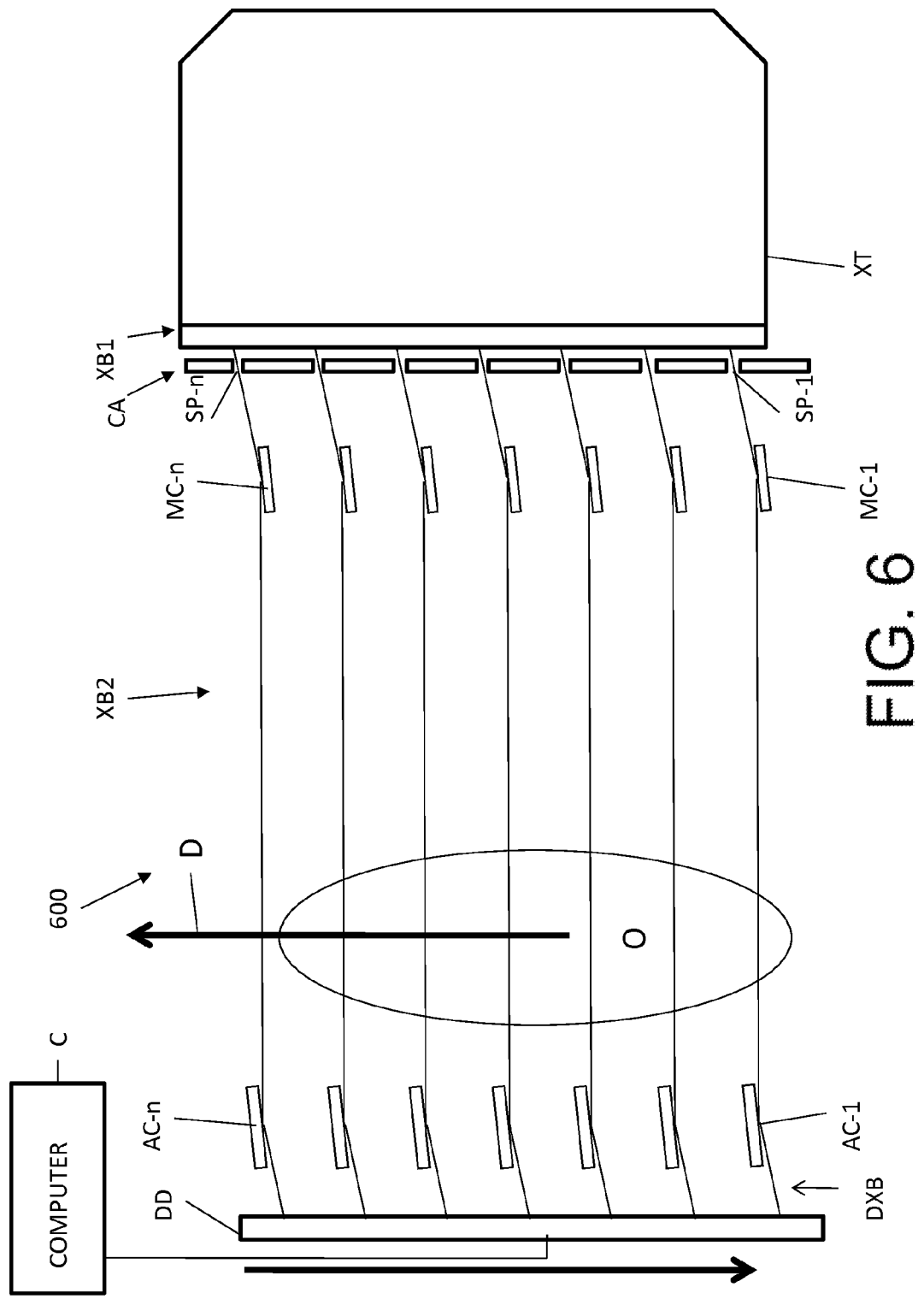

Referring now to FIG. 6, another example DEI system 600 for detecting an image of the object O according to an embodiment of the subject matter disclosed herein is shown. DEI system 600 is similar to DEI system 100 shown in FIG. 1 except that, rather than the use of multiple X-ray tubes XT-1-XT-n, system 600 includes a single X-ray tube XT having multiple source points SP-1-SP-n, each capable of functioning as a small area source. Therefore, X-ray tube XT can produce a plurality of X-ray beams, generally designated XB1. The system 600 may also include a collimator array CA positioned near the X-ray tube XT.

Figure 7:
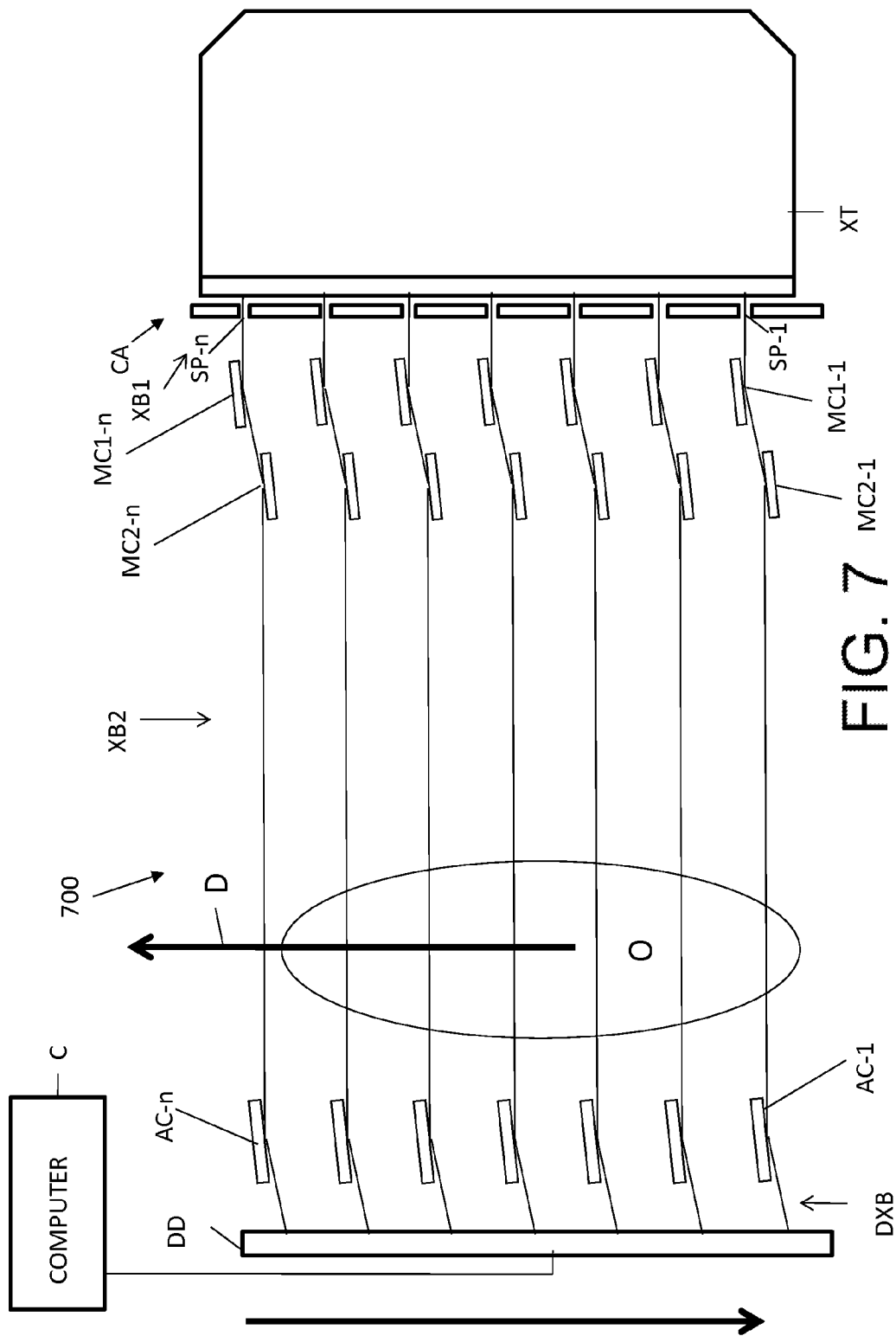

Referring now to FIG. 7, another example DEI system 700 for detecting an image of the object O according to an embodiment of the subject matter disclosed herein is shown. DEI system 700 is similar to DEI system 500 shown in FIG. 5 and DEI system 600 shown in FIG. 6. Similar to system 500 shown in FIG. 5, system 700 includes monochromator crystals MC1-1-MC1-n and MC2-1-MC2-n. Further, similar to system 600 shown in FIG. 6, system 700 includes a single X-ray tube XT having multiple source points SP-1-SP-n, each capable of functioning as a small area source for producing X-ray beams XB1.

Figure 8:
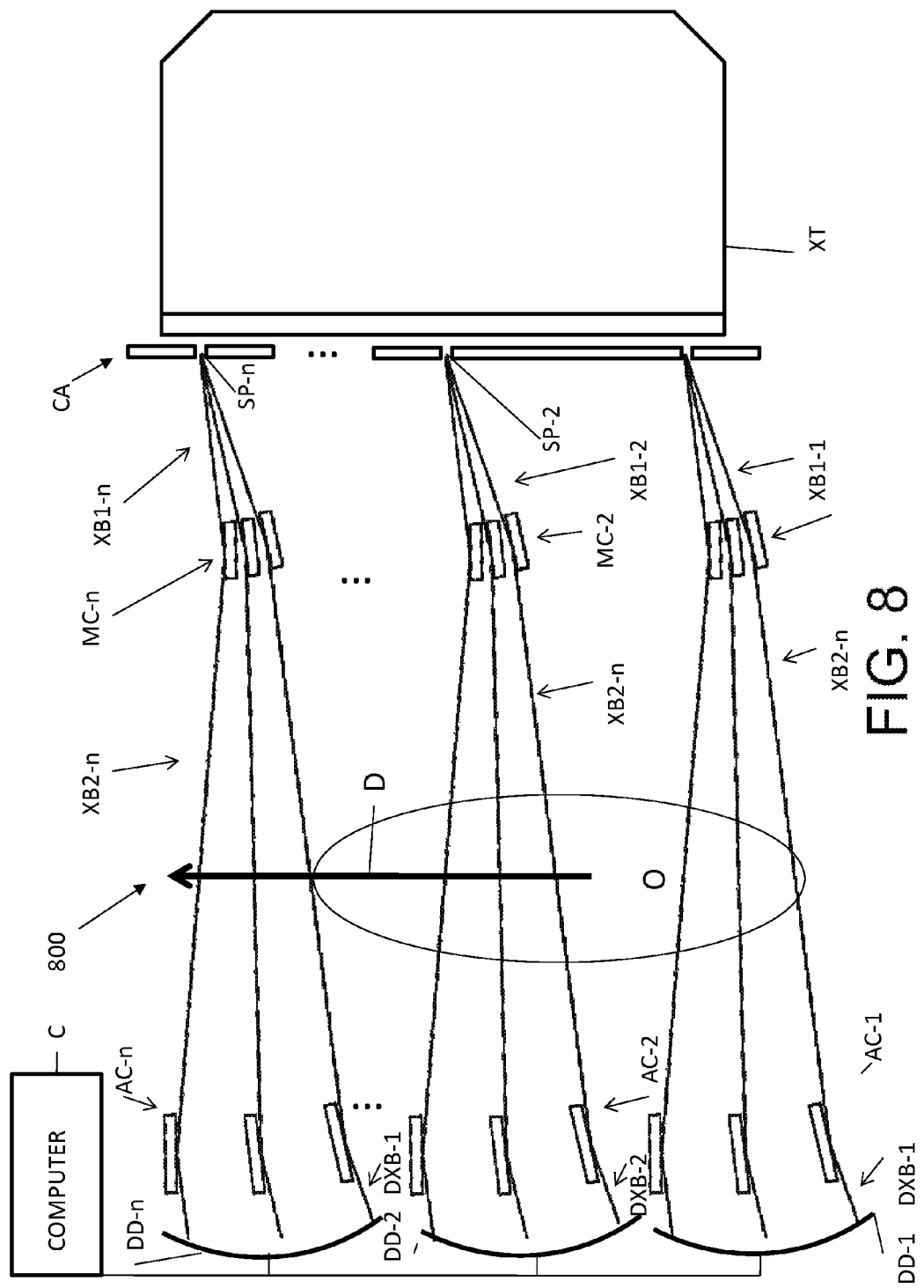

Referring now to FIG. 8, another example DEI system 800 for detecting an image of the object O according to an embodiment of the subject matter disclosed herein is shown. DEI system 800 is similar to DEI system 600 shown in FIG. 6 except that the source points SP-1-SP-n of system 800 each emit an X-ray beam XB that fans out toward sets of monochromator crystals MC-1-MC-n. For example, source points SP-1 and SP-n emit fanning X-ray beams, generally designated XB1-1 and XB1-n, respectively, directed to the sets of monochromator crystals MC-1 and MC-n, respectively. In turn, X-ray beam sets XB2-1-XB2-n, originating from the monochromator crystals, are directed towards the analyzer crystal sets AC-1-AC-n.

System 800 includes a plurality of digital detectors DD-1-DD-n each configured to receive respective, diffracted X-ray beams DXB-1-DXB-n from the analyzer crystal sets AC-1-AC-n. Computer C is operable to receive electrical signals from the digital detectors DD-1-DD-n for generating an image of the object O.

Figure 9:
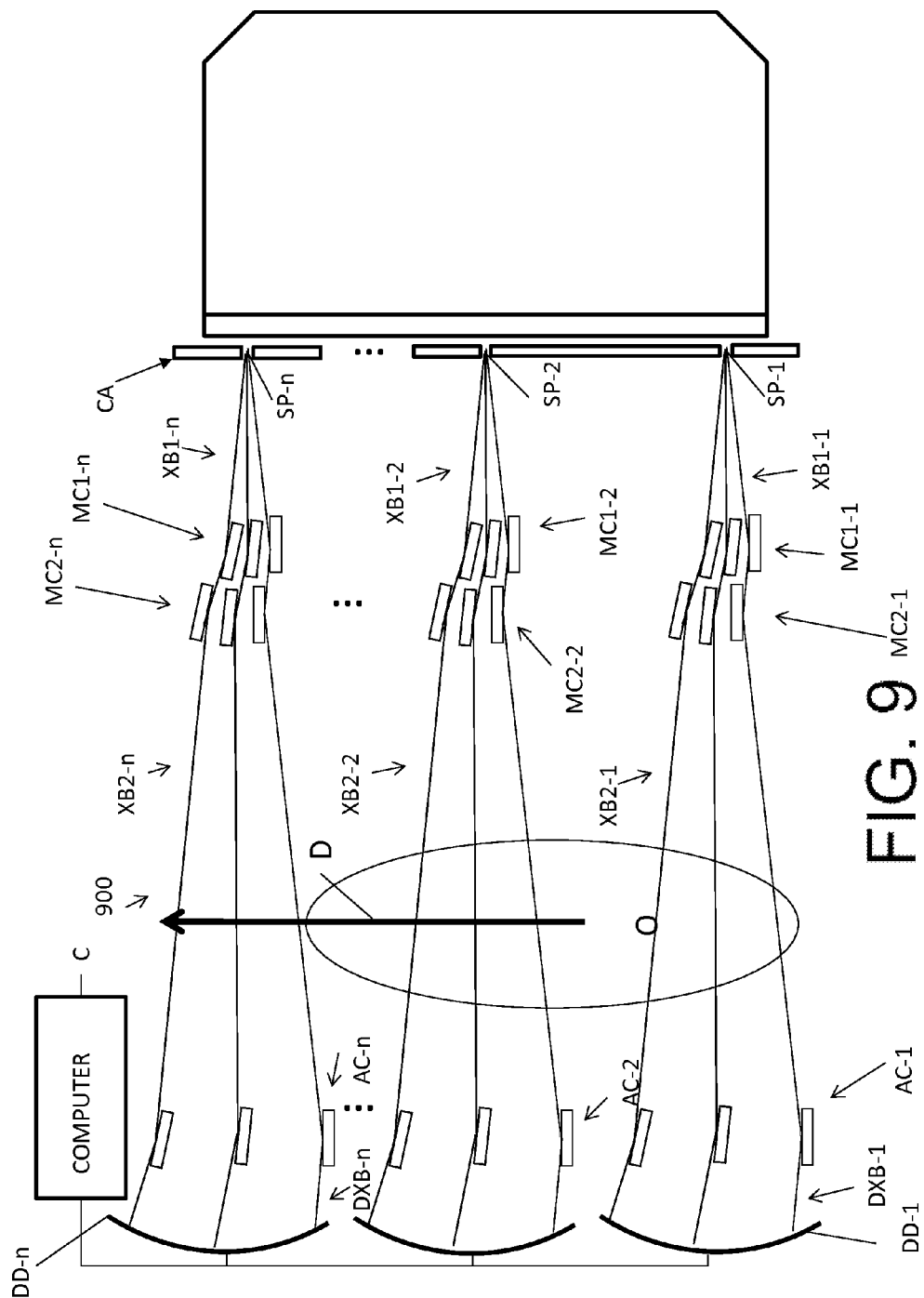

Referring now to FIG. 9, another example DEI system 900 for detecting an image of the object O according to an embodiment of the subject matter disclosed herein is shown. DEI system 900 is similar to DEI system 800 shown in FIG. 8 except that system 900 includes monochromator crystals MC1-1-MC1-n and MC2-1-MC2-n similar to DEI system 500 shown in FIG. 5.

Figure 10:
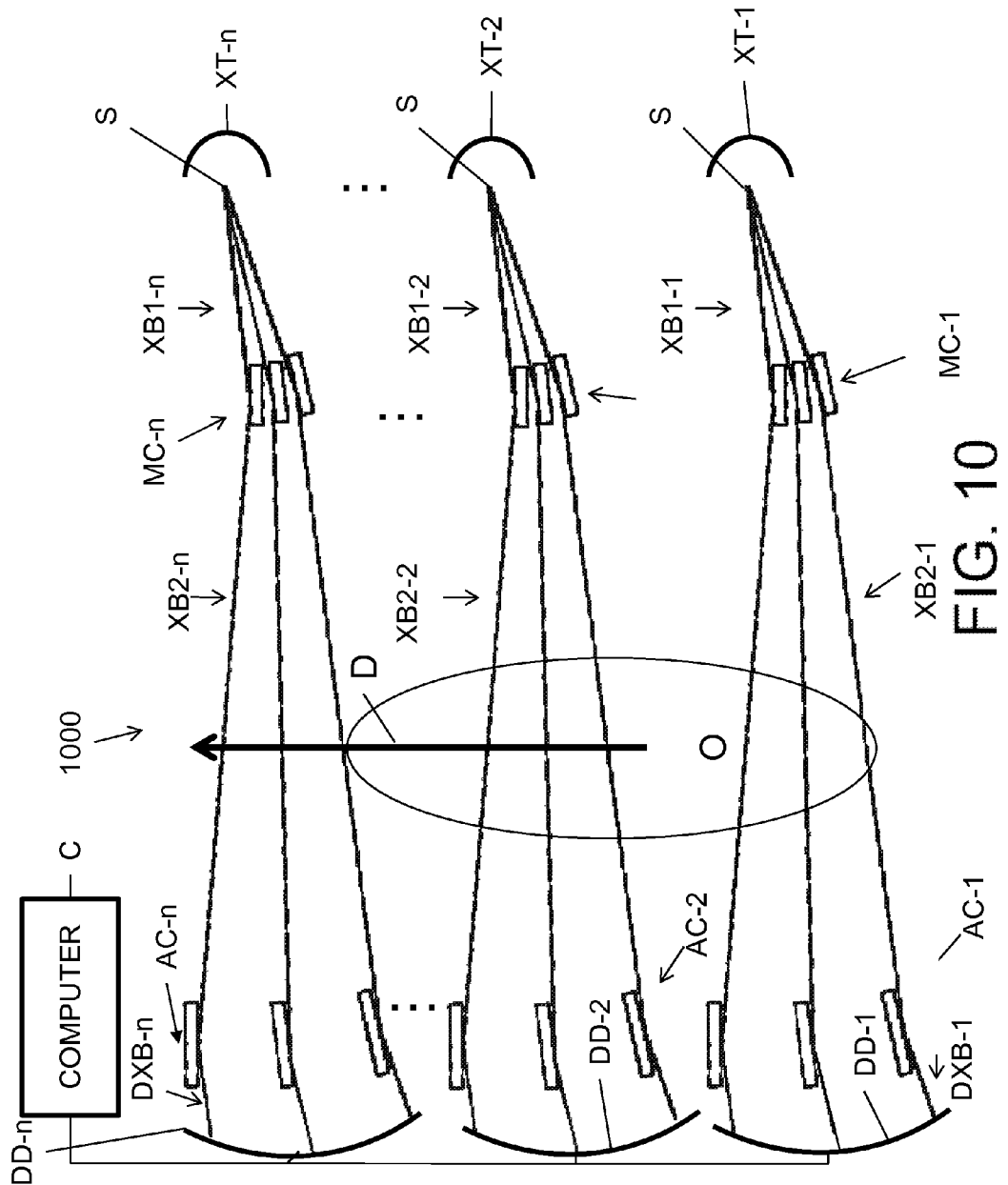

Referring now to FIG. 10, another example DEI system 1000 for detecting an image of the object O according to an embodiment of the subject matter disclosed herein is shown. DEI system 1000 is similar to DEI system 800 shown in FIG. 8 except that system 1000 includes X-ray tubes XT-1-XT-n similar to the DEI system 500 shown in FIG. 5.

Figure 11:
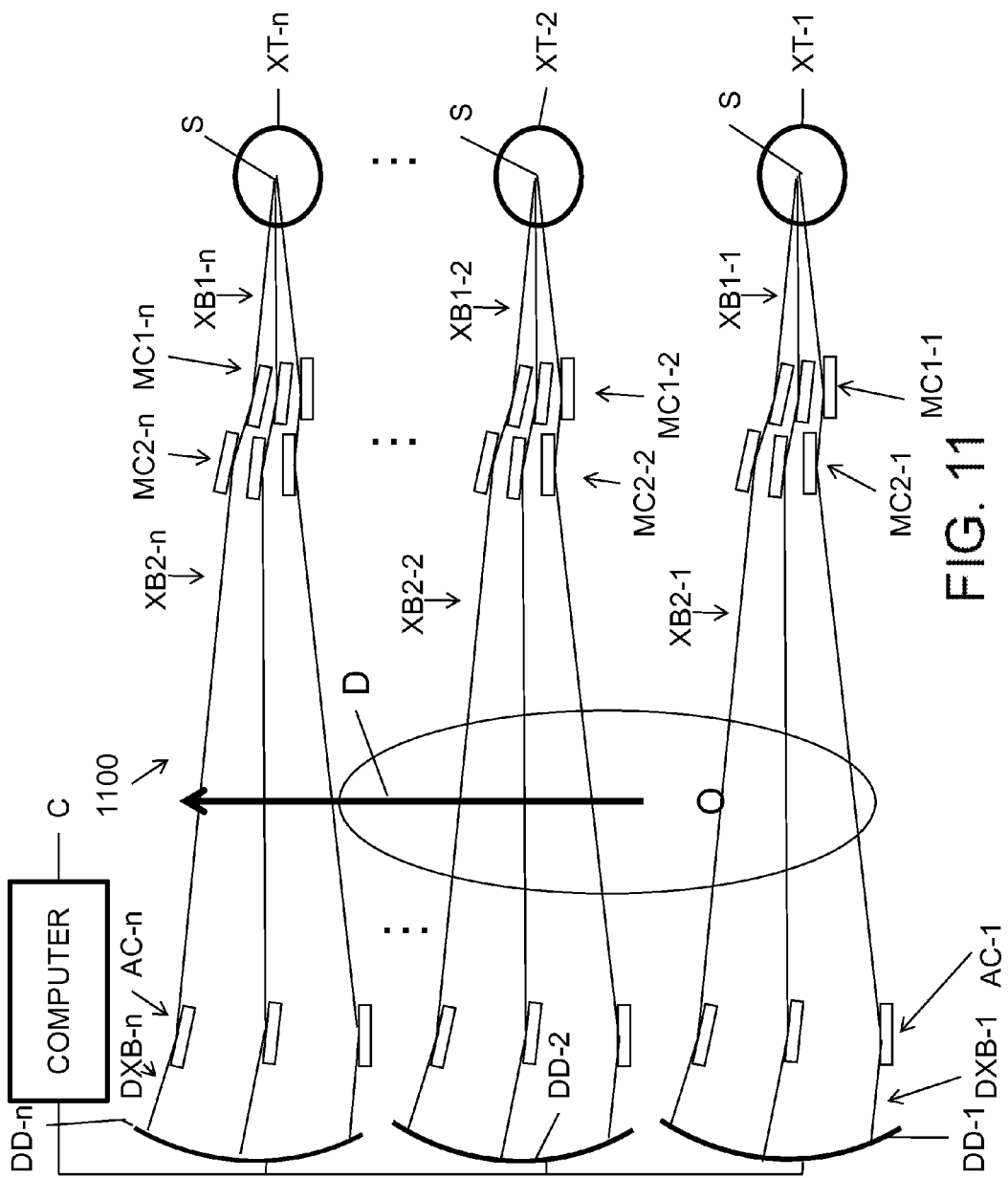

Referring now to FIG. 11, another example DEI system 1100 for detecting an image of the object O according to an embodiment of the subject matter disclosed herein is shown. DEI system 1100 is similar to DEI system 900 shown in FIG. 9 except that the source points originate from different X-ray tubes XT-1-XT-n similar to the DEI system 500 shown in FIG. 5.

Crystal Strain Matching

The monochromator and analyzer crystals can strain under their own weight, which result in changes in the lattice spacing of the crystals. Because the reflection energy and angle are dependent upon the lattice spacing of the crystal, variations in the lattice spacing of the crystals can lead to misaligned, or even unalignable optics. The surfaces of the crystals may be strain-matched so that any X-ray from a diverging X-ray beam "sees" the same crystal lattice spacing at each reflection. This can be accomplished by varying the crystal cross-section as a function of the beam size on the optics.

In their simplest form, equations for prefect crystal diffraction require constant lattice spacing. Practically, crystal strains, causing variations in lattice spacing, are unavoidable. The strain can be from thermal variations within the crystal or from mechanical loads on the crystal. While the thermal variations can be mitigated through strict temperature controls, mechanical strains are unavoidable. Because of the extremely fine angular and energy sensitivity of perfect crystal optics, variations in the lattice spacing on the order of 0.005% can lead to intensity variations in the DEI system on the order of 50%.

Figure 13:
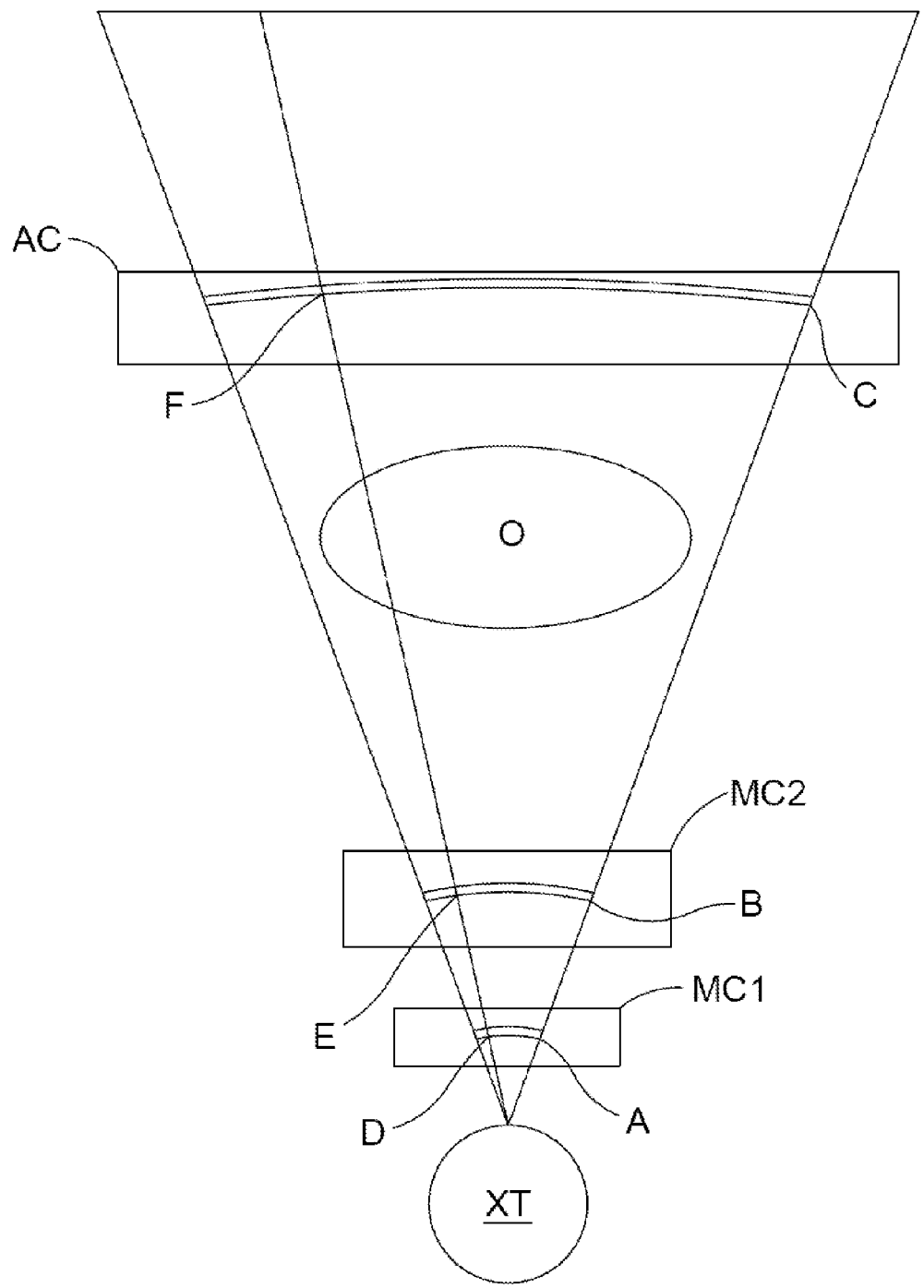
FIG. 13 is a top view of an arrangement of monochromator crystals and an analyzer crystal having strain-matching in a DEI system according to an embodiment of the subject matter described herein.
Figure 14:
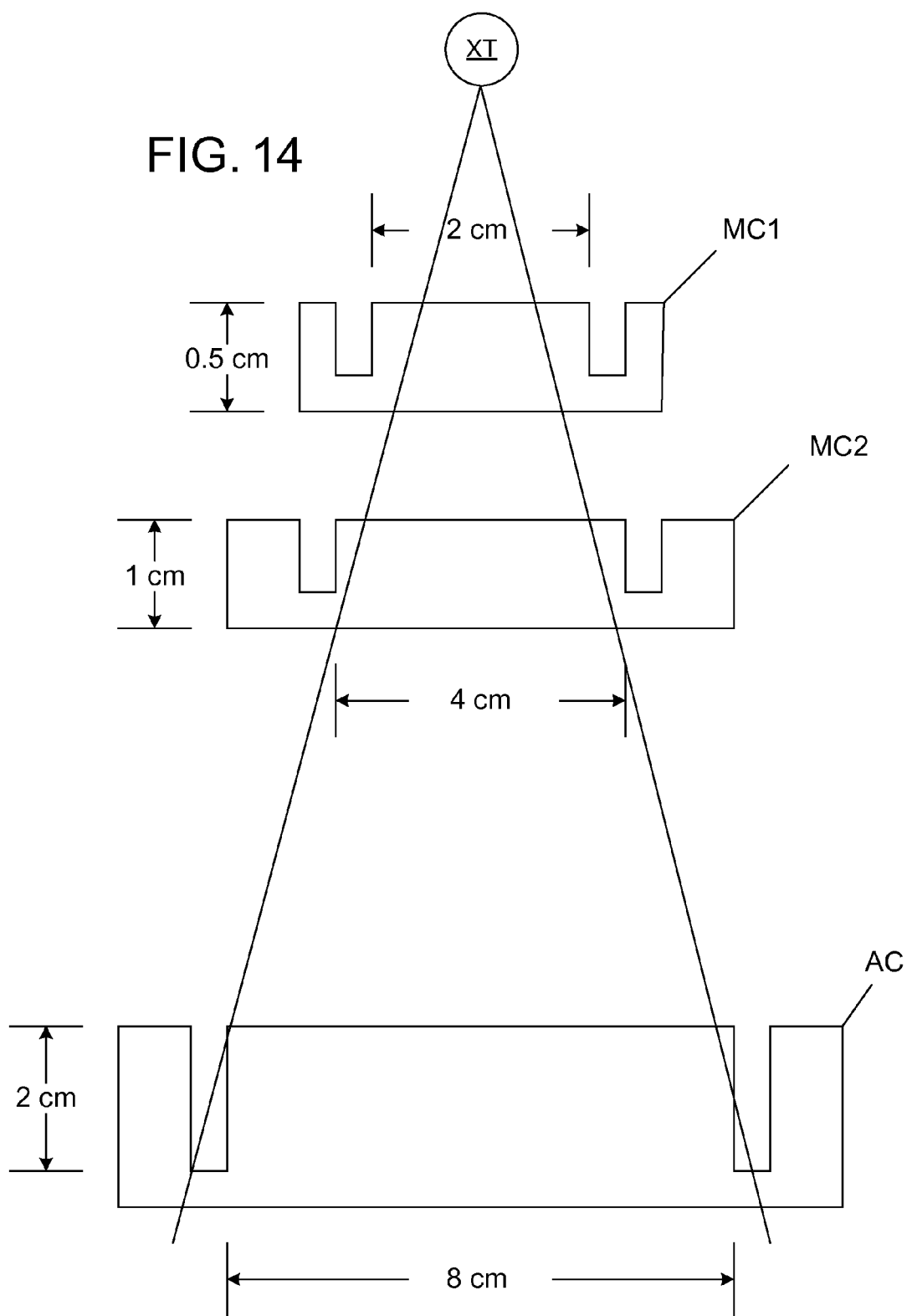
FIG. 14 is a cross-section view of the monochromator crystals and the analyzer crystal shown in FIG. 13.

The subject matter disclosed herein solves this problem by allowing for strain along the crystal face, but vary the vertical and horizontal cross-section of the crystals to match that strain along any beam within the system. With an x-ray tube-based DEI system such as system 500 shown in FIG. 5, the beam is divergent along the horizontal direction. For example, FIG. 13 shows a top view of a DEI system with divergent X-ray beams emitting from an X-ray tube XT. Referring to FIG. 13, in order to have each of the diverging beams (e.g. beam ABC or beam DEF) see a constant lattice spacing along each of the crystal faces, then the vertical and horizontal cross-section of each crystal must be varied. This can be achieved by scaling the crystals' vertical and horizontal cross-sections with the beam size on the crystal. For example, if the horizontal beam size is 2 cm on the first monochromator crystal MC1, 4 cm on the second monochromator crystal MC2, and 8 cm on the analyzer crystal AC, and the first monochromator crystal MC1 has a height of 0.5 cm, then the second monochromator crystal MC2 may have a height of 1 cm, and the analyzer crystal AC should have a height of 2 cm. In this example, the ratio between the beam size along one dimension and the crystal size along the same dimension remains constant. It should be noted that the crystals and X-ray beam shown in FIG. 13 are not to scale. FIG. 14 shows cross-sectional views of each of the crystals MC1, MC2, and AC.

Figure 15:
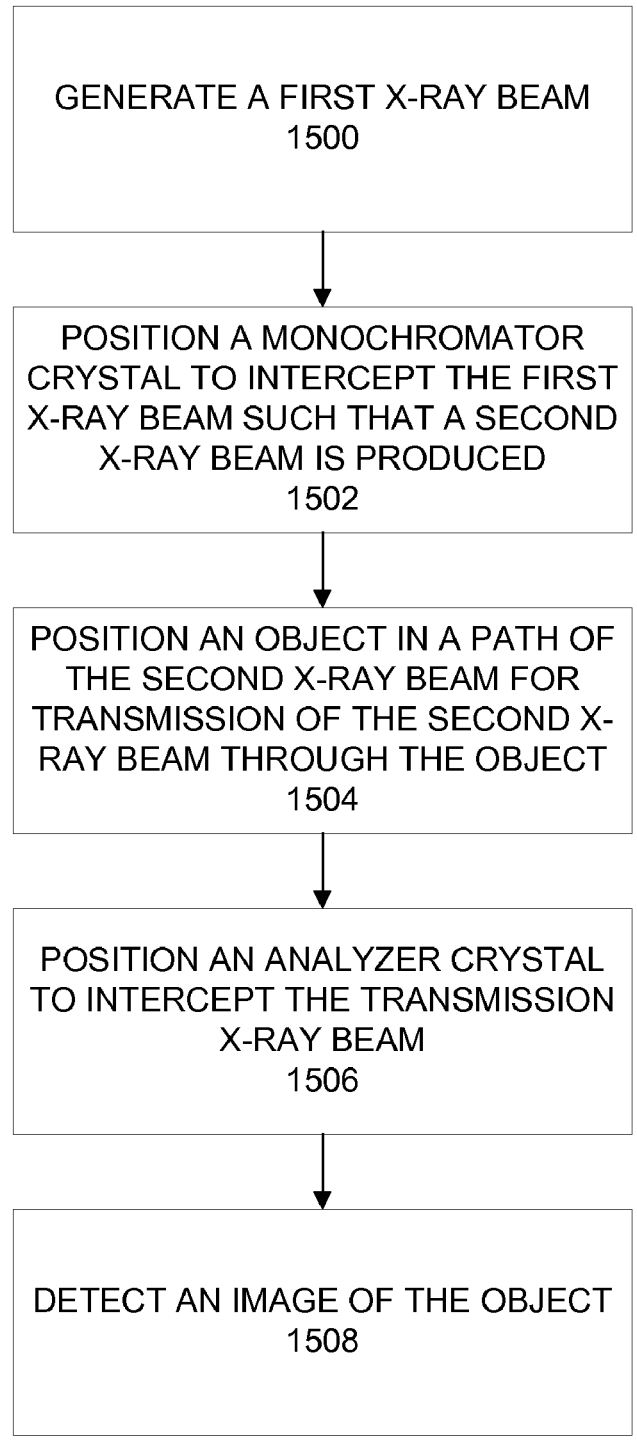
FIG. 15 is a flow chart of an exemplary process for imaging an object by use of a DEI system, such as the DEI system shown in FIGS. 13 and 14, according to an embodiment of the subject matter described herein.

FIG. 15 is a flow chart illustrating an exemplary process for imaging an object by use of a DEI system, such as the DEI system shown in FIGS. 13 and 14, according to an embodiment of the subject matter described herein. Referring to FIG.

15, in step 1500, a first X-ray beam is generated. For example, X-ray tube XT shown in FIG. 13 can generate an X-ray beam. At step 1502, a monochromator crystal may be positioned to intercept the first X-ray beam such that a second X-ray beam is produced. For example, one or more the monochromator crystals (such as monochromator crystals MC1 and MC2 shown in FIG. 13) can be positioned to intercept the X-ray beam generated by an X-ray tube XT.

At step 1504, an object (such as object O shown in FIG. 13) is positioned in a path of the second X-ray beam for transmission of the second X-ray beam through the object and for emitting from the object a transmission X-ray beam. An analyzer crystal can be positioned to intercept the transmission X-ray beam at angles of incidence of the analyzer crystal (step 1506). For example, the analyzer crystal AC can be positioned to intercept the beams transmitted through the object O. At step 1508, a detector may detect an image of the object from one or more beams diffracted from the analyzer crystal.

Horizontally-Spaced Monochromator and Analyzer Crystal Arrays

In order to have a clinically useful, general purpose DEI system, it is desirable to provide a field of view for imaging that is about 36 cm by 43 cm, or greater. A concern of providing field of view on this scale is that a crystal of this width will have surface straining sufficient to cause it to be virtually impossible to fully align the system across the full width of the beam. Additionally, there is a concern that it could be cost-prohibitive to use x-ray optics of this size. Through the use of arrays of vertically-offset, horizontal x-ray beams, a horizontally large x-ray beam can be created using horizontally small monochromator and analyzer crystals for solving these and other issues.

In their simplest form, equations for prefect crystal diffraction require a constant lattice spacing. In reality though, crystal strains, causing variations in lattice spacing, are unavoidable. The strain can be from thermal variations within the crystal or from mechanical loads on the crystal. Because of the extremely fine angular and energy sensitivity of perfect crystal optics, variations in the lattice spacing on the order of 0.005% can lead to intensity variations in the DEI system on the order of 50%. There are common techniques practiced within the synchrotron research community to minimize the strain gradients along the face of perfect crystal optics, including making strain cuts along the edges of crystals and placing the mechanical support outside of the strain cuts. Though this technique works for smaller crystals, it is not clear to what extent the strain can be reduced along the crystal face when crystals as large as 40 cm are being implemented.

Figure 16:
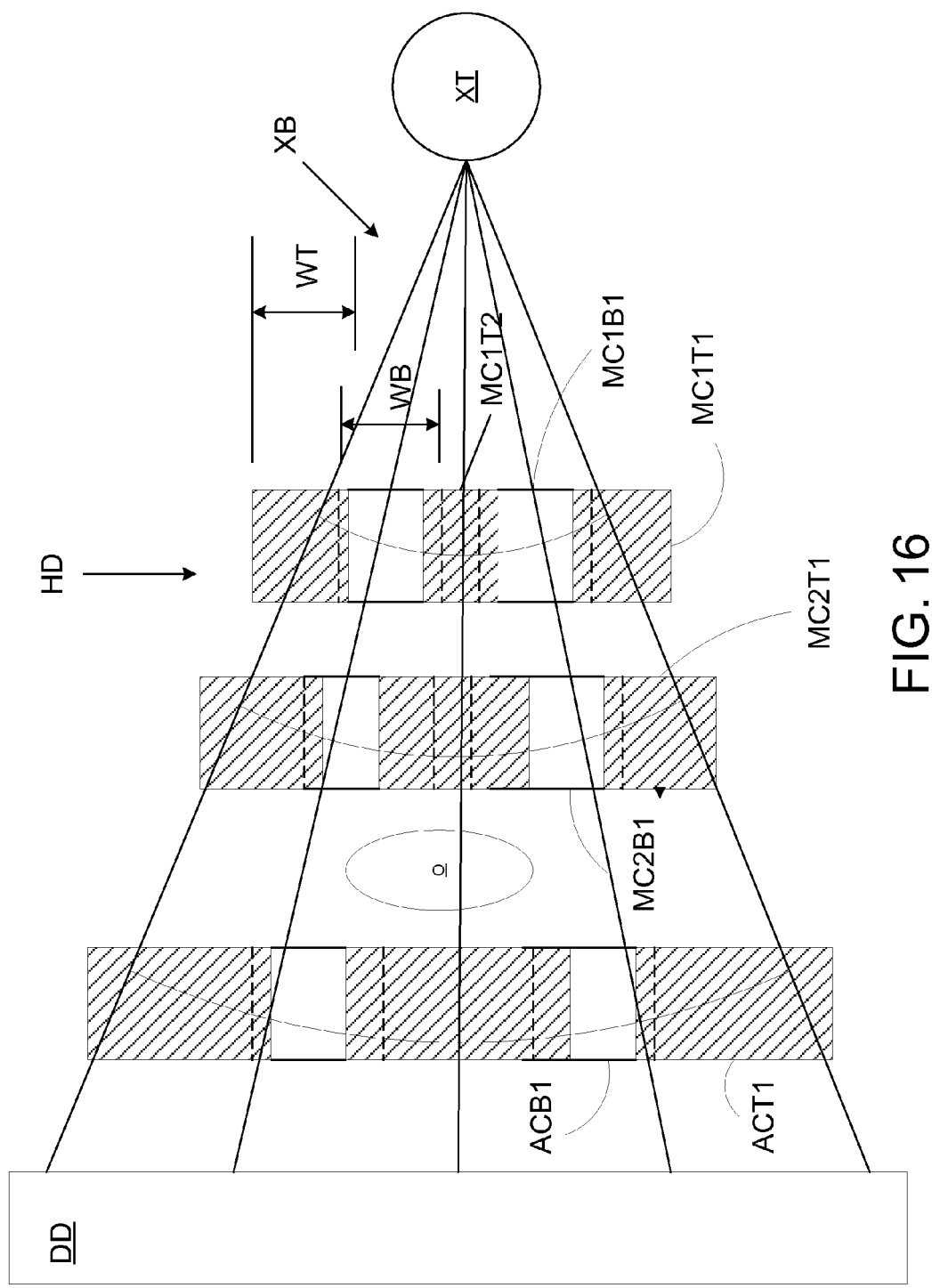
FIG. 16 is a top view of a DEI system including horizontally-spaced monochromator and analyzer crystal arrays according to an embodiment of the subject matter described herein.
Figure 17:
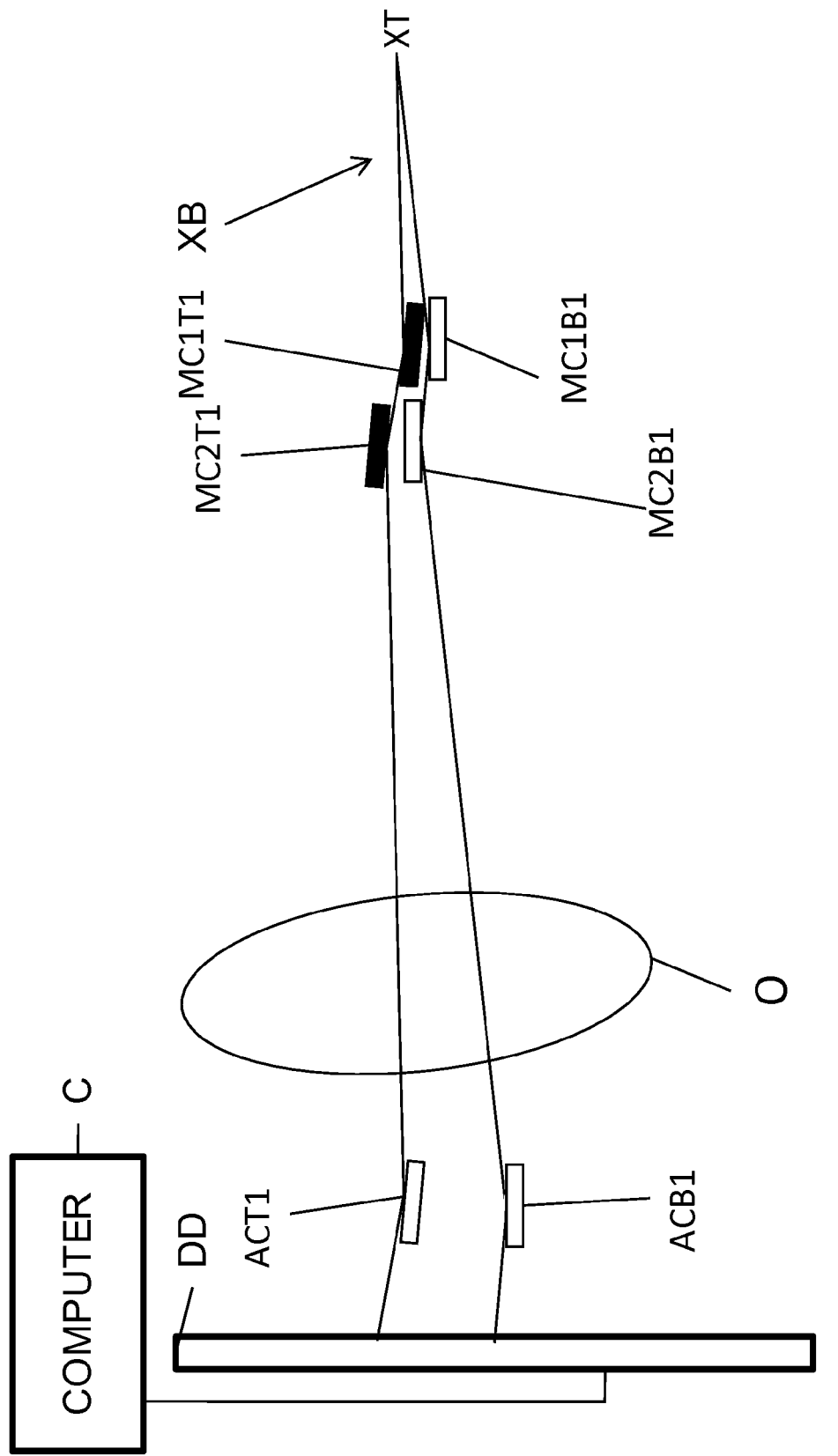
FIG. 17 is a side view of the DEI system shown in FIG. 15.

FIGS. 16 and 17 illustrate different views of an exemplary DEI system for solving the above-described difficulties. In this example, the horizontally large crystals in other DEI systems are replaced with a horizontal array of smaller crystals. Referring to FIGS. 16 and 17, the DEI system includes a horizontal array of monochromator crystals MC1T1 and MC2T1, monochromator crystal MC1B1, monochromator crystals MC2T1 and MC2B1, and analyzer crystals ACT1 and ACB1. Gaps or spacings are provided between the arrays of crystals along a substantially horizontal direction HD. In order to overcome this, the adjacent crystals in the horizontal array will be vertically offset from one another.

Monochromator crystals MC1T1 and MC2T1 (indicated by diagonal markings) are positioned above monochromator crystals MC1B1 and MC2B1, respectively. An X-ray beam XB emitted by X-ray tube XT can be intercepted by top surfaces of monochromator crystals MC1T1, and MC1B1.

The top surfaces of these monochromator crystals can overlap one another in the direction HD such that there is no spacings of crystal surface in the direction HD. The intercepted X-ray beam XB can then be redirected by monochromator crystals MC1T1 and MC1B1 to respective monochromator crystals MC2B1 and MC2T1. Reference indicia WB and WT indicate the widths of the bottom crystal and the top crystal, respectively.

Similar to monochromator crystals MC1T1 and MC1B1, monochromator crystals MC2B1 and MC2T1 and the other monochromator crystals aligned in the direction HD can be spaced apart such that there is no spacings of crystal surface in the direction HD. The monochromator crystals MC2B1 and MC2T1 can redirect the X-ray beam XB for transmission through an object O. The detector can detect an image of the object from beams diffracted from the analyzer crystals as described in further detail herein.

Figure 18:
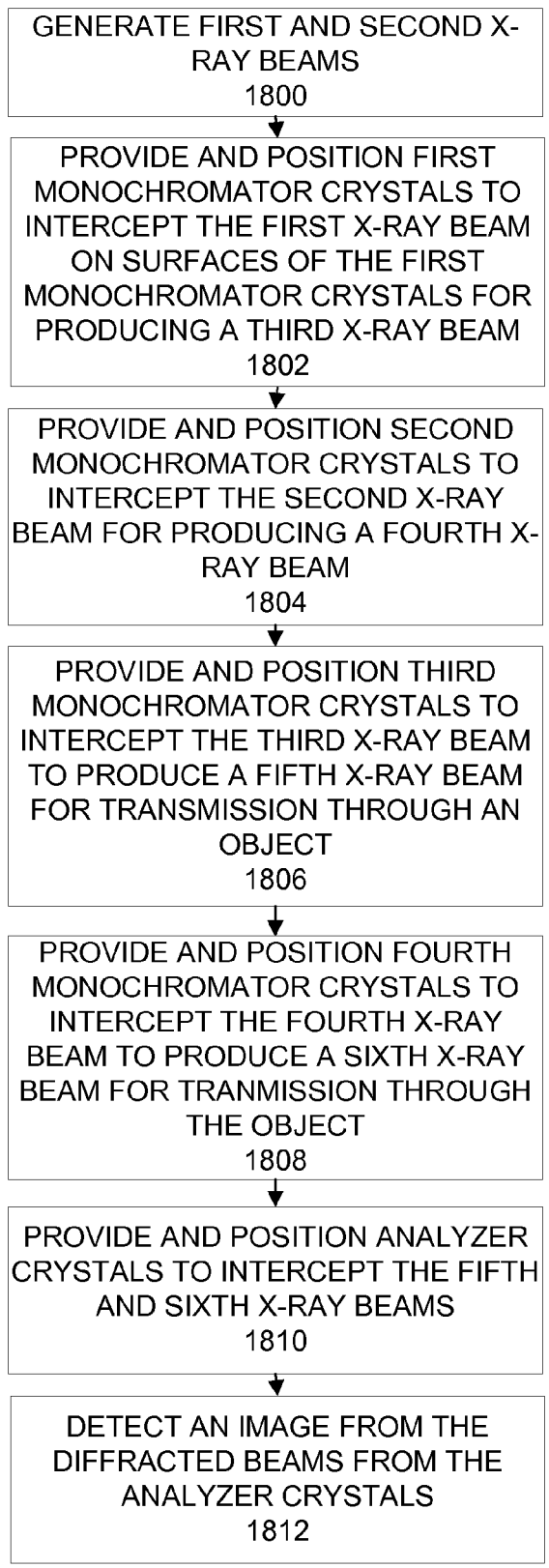
FIG. 18 is a flow chart of an exemplary process for imaging an object by use of a DEI system, such as the DEI system shown in FIGS. 16 and 17, according to an embodiment of the subject matter described herein.

FIG. 18 is a flow chart of an exemplary process for imaging an object by use of a DEI system, such as the DEI system shown in FIGS. 16 and 17, according to an embodiment of the subject matter described herein. Referring to FIG. 18, at step 1800, first and second X-ray beams are generated. For example, X-ray tube XT, shown in FIG. 17, can produce X-ray beams.

At step 1802, first monochromator crystals are provided that are spaced apart substantially along a first direction. Further, at step 1802, the first monochromator crystals are positioned to intercept the first X-ray beam on surfaces of the first monochromator crystals for producing a third X-ray beam. For example, referring to FIG. 17, monochromator crystals MC1T1 can be provided for intercepting an X-ray beam from X-ray tube XT and for generating another X-ray beam.

At step 1804, second monochromator crystals are provided that are spaced apart substantially along the first direction. Further, at step 1804, the second monochromator crystals are positioned to intercept the second X-ray beam on surfaces of the second monochromator crystals for producing a fourth X-ray beam. For example, referring to FIG. 17, monochromator crystals MC1B1 can be provided for intercepting an X-ray beam from X-ray tube XT and for generating another X-ray beam.

At step 1806, third monochromator crystals are provided that are spaced apart substantially along the first direction. Further, at step 1806, the third monochromator crystals are positioned to intercept the third X-ray beam on surfaces of the third monochromator crystals to produce a fifth X-ray beam for transmission through an object. For example, monochromator crystals MC2T1 can be positioned to intercept the X-ray beam from monochromator crystals MC1T1 to produce another X-ray beam.

At step 1808, fourth monochromator crystals are provided that are spaced apart substantially along the first direction. Further, at step 1808, the fourth monochromator crystals are positioned to intercept the fourth X-ray beam on surfaces of the fourth monochromator crystals to produce a sixth X-ray beam for transmission through the object. For example, monochromator crystals MC2B1 can be positioned to intercept the X-ray beam from monochromator crystals MC1B1 to produce another X-ray beam.

At step 1810, analyzer crystals are provided and positioned to intercept the fifth and sixth X-ray beams at angles of incidence of the analyzer crystals. For example, analyzer crystals ACT1 and ACB1 shown in FIG. 17 can be positioned to intercept X-ray beams from monochromator crystals MC2T1 and MC2B1, respectively. At step 1812, an image of the object is detected from beams diffracted from the analyzer crystals. For example, detector DD can detect the image of object O from the beams diffracted from analyzer crystals MC2T1 and MC2B1.

Figure 19:
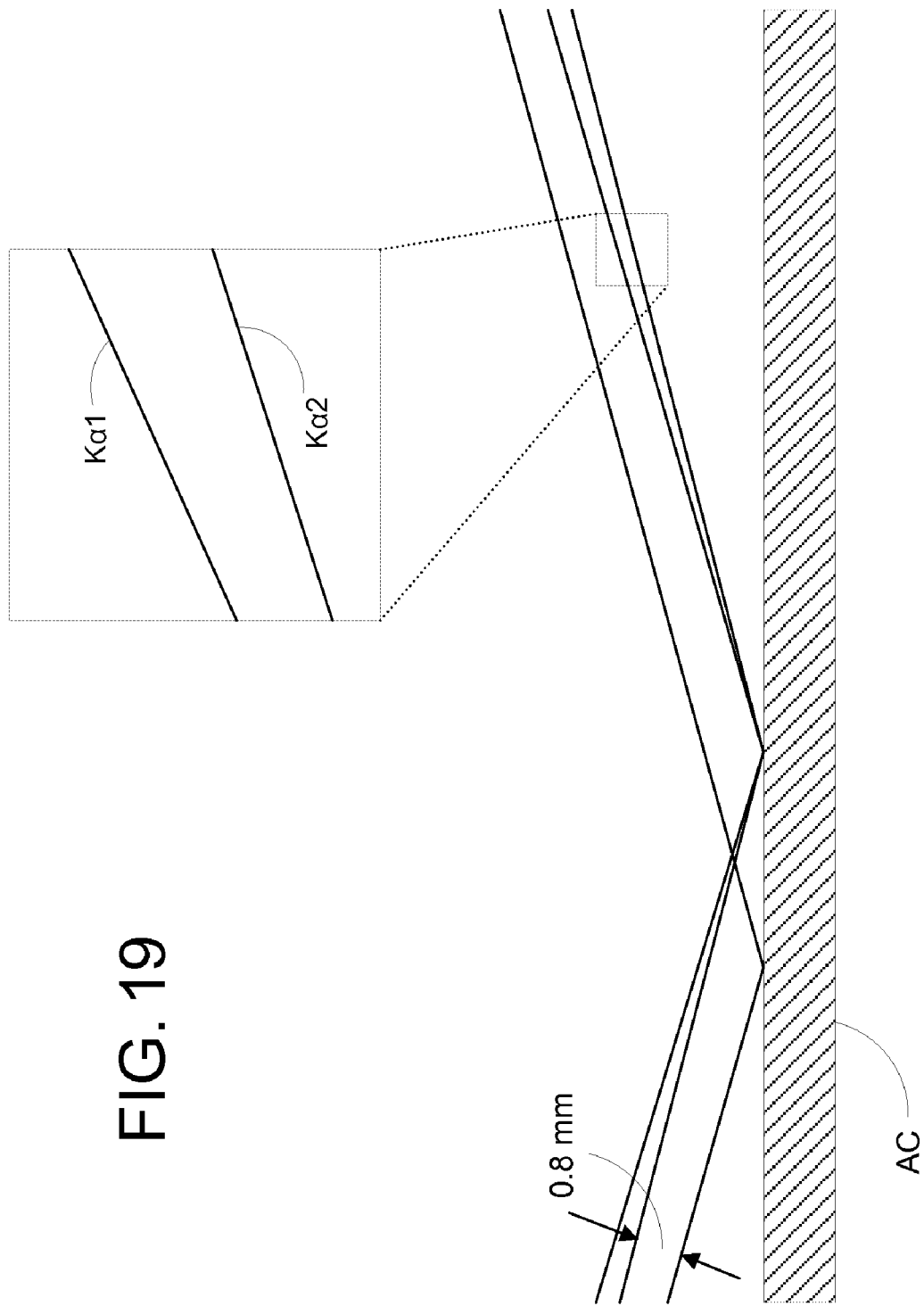
FIG. 19 is a side view of an analyzer crystal of any one of the DEI systems shown in FIGS. 1-11, 16, and 17 according to an embodiment of the subject matter described herein.

FIG. 19 is a side view of analyzer crystal AC of any one of the DEI systems shown in FIGS. 1-11, 16, and 17 according to an embodiment of the subject matter described herein. Referring to FIG. 19, the diffraction of characteristic emission lines Kα1 and Kα2 from the surface of analyzer crystal AC are shown. The accommodation of more than one x-ray energy can result in improved X-ray flux.

In another embodiment, a DEI system in accordance with the subject matter described herein can include a mismatch crystal design for rejecting particular X-rays emitted by an X-ray tube. In this design, the Kα2 emission line of the X-ray beam can be eliminated at the monochromator. A collimator can be positioned for blocking a portion of an X-ray beam that fall outside an angular acceptance window of a first monochromator crystal, such as, for example, one of monochromator crystals MC1-1-MC1-*n*. The unblocked portion of the X-ray beam can intercept the first monochromator crystal, which refracts the unblocked portion in a direction for intercept by a second monochromator crystal, such as, for example, one of monochromator crystals MC2-1-MC2-*n*. The first monochromator crystal can be tuned to a particular angle using Bragg's Law to select a very narrow range of photon energies for resulting in a diffracted monochromatic beam directed towards the second monochromator crystal. Because of the divergence of the X-ray beam from a source point, the first monochromator crystal can diffract a range of energies which can include the characteristic emission lines Kα1 and Kα2 and bremsstrahlung radiation at nearby energies. A function of the second monochromator crystal is to redirect the beam to a direction parallel to the incident beam and aligned with the analyzer crystal. When tuning the system for a particular energy, the first monochromator crystal is aligned first, and then the second crystal is tuned to find the position of the beam.

With the second monochromator crystal aligned, the analyzer crystal is scanned to find the position of the beam on the crystal. Rocking the crystal to find the beam position is analogous to scanning a radio dial to find a particular station, generating a sharp rise in intensity when the angular position of the analyzer is in perfect alignment with the second monochromator crystal. Once the analyzer crystal is aligned, the system is tuned and ready for use.

The first and second monochromator crystals, respectively, can be configured in a mismatch crystal design for rejecting particular X-ray beams emitted by a source point, such as a source point of an X-ray tube. The monochromator crystals can be used to eliminate the Kα2 emission line of the X-ray beam, which can be achieved by utilizing the angular acceptance versus energy for different crystals. In one example, the monochromator crystals can be germanium [333] and silicon [333] monochromator crystals, respectively.

In another example of detecting the image of the object, a first angle image of object O can be detected from a first diffracted beam emitted from an analyzer crystal positioned at a first angular position. The first angle image of an object can be detected at a low rocking curve angle setting of the analyzer crystal. Further, a second angle image of the object can be detected from a second diffracted beam emitted from the analyzer crystal positioned at a second angular position. The second angle image of the object can be detected at a high rocking curve angle setting of the analyzer crystal. The first and second angle images can be combined by a computer to derive a refraction image. Further, the computer can derive a mass density image of the object from the refraction image. The mass density image can be presented to a user via a display of the computer.

Figure 20:
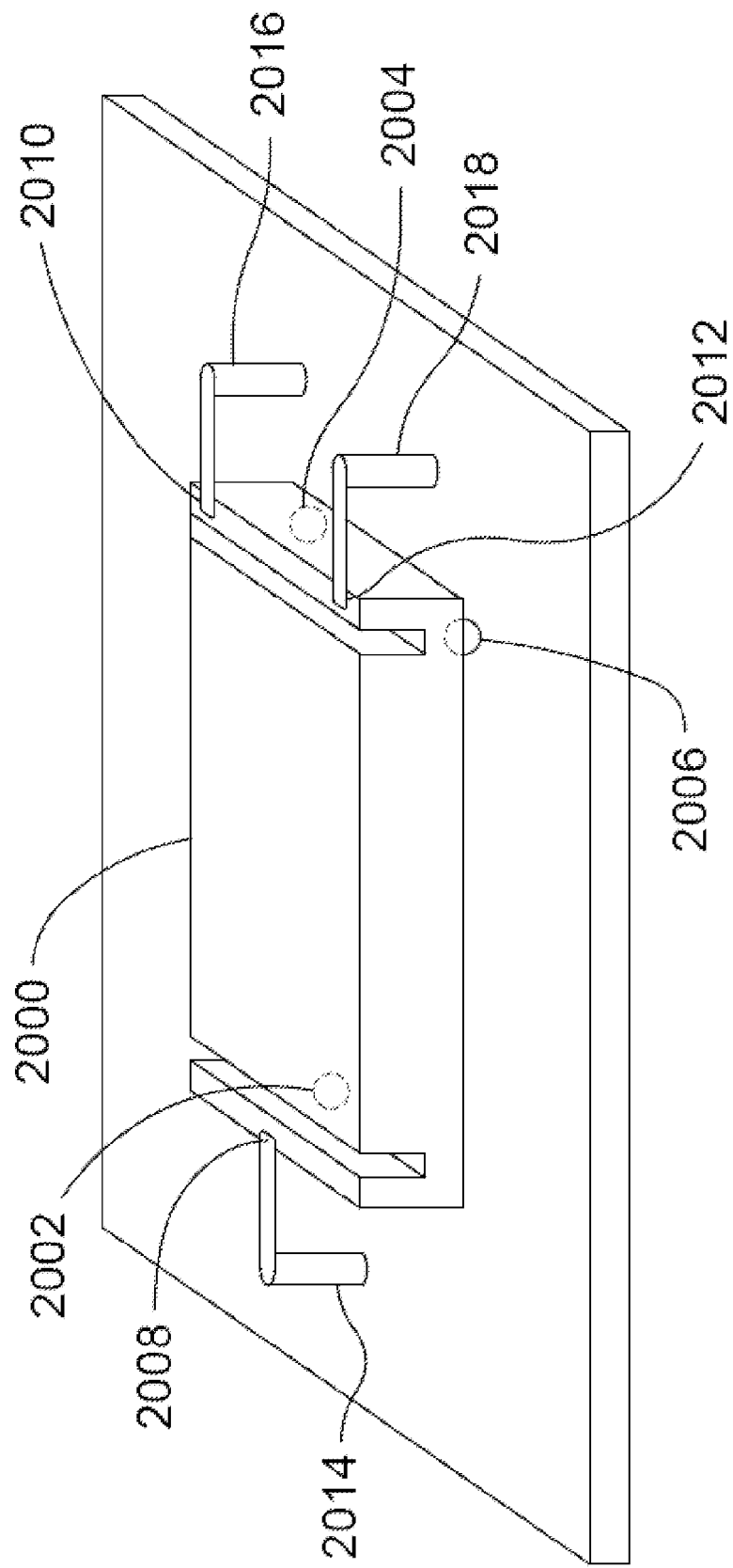
FIG. 20 is a perspective view of a crystal 2000 being supported at a plurality of points for three-dimensional bowing in accordance with an embodiment of the subject matter described herein.

Monochromator and analyzer crystals in accordance with embodiments of the subject matter described herein may be scaled in one or more directions. Particularly, the crystals may be manipulated to deform or bow two-dimensionally or three-dimensionally. FIG. 20 is a perspective view of a crystal 2000 being supported at a plurality of points for three-dimensional bowing in accordance with an embodiment of the subject matter described herein. Referring to FIG. 20, the crystal 2000 rests on ball bearings 2002, 2004, and 2006, which correspond to support tips 2008, 2010, and 2012, respectively, on support structures 2014, 2016, and 2018, respectively. The crystal 2000 is supported at a few points such that there will be bowing of the crystal 2000 relative to the support points. Thickness of the crystal may be varied to adjust bowing.

Exemplary Applications

The systems and methods in accordance with the subject matter described herein can be applied to a variety of medical applications. As set forth above, the systems and methods described herein can be applied for breast imaging. Further, for example, the systems and methods described herein can be applied to cartilage imaging, neuroimaging, cardiac imaging, vascular imaging (with and without contrast), pulmonary (lung) imaging, bone imaging, genitourinary imaging, gastrointestinal imaging, soft tissue imaging in general, hematopoietic system imaging, and endocrine system imaging. In addition to image time and dose, a major advancement of using higher energy X-rays is the thickness of the object that can be imaged. For applications such as breast imaging, the system described allows for imaging full thickness breast tissue with a clinically realistic imaging time. The same can be said for other regions of the body, such as the head, neck, extremities, abdomen, and pelvis. Without the limitations of X-ray absorption, utilization of DEI with higher energy X-rays dramatically increases the penetration ability of X-rays. For soft tissue, only a small portion of the X-ray photons incident on the object are absorbed, which greatly increases efficiency of emitted photons from the X-ray tube reaching the detector.

With respect to pulmonary imaging, DEI techniques as described herein can produce excellent contrast in the lungs and can be used heavily for diagnosing pulmonary conditions such as pneumonia. Fluid collections in the lungs generate a marked density gradient that could be detected easily with DEI. The density gradient, characteristics of the surrounding tissue, and geometric differences between normal lung tissue and tissue with a tumor can be large, producing good contrast. Further, DEI techniques described herein can be applied to lung cancer screening and diagnosis.

With respect to bone imaging, DEI techniques as described herein can produce an excellent image of bone in general. High refraction and extinction contrast of DEI can be especially useful for visualizing fractures and lesions within the bone.

Further, the systems and methods in accordance with the subject matter described herein can be applied to a variety of inspection and industrial applications. For example, the systems and methods can be applied for meat inspection, such as poultry inspection. For example, the systems and methods can be used for viewing sharp bones, feathers, and other low contrast objects in meats that required screening and/or removal. The systems and methods described herein can be applied for such screening.

The systems and methods described herein can also be applied for manufacture inspection. For example, the systems and methods can be used for inspecting welds, such as in aircraft production. DEI techniques as described herein can be used to inspect key structural parts that undergo heavy wear and tear, such as jet turbine blades. Further, for example, the systems and methods described herein can be used for inspecting circuit boards and other electronics. In another example, the systems and methods described herein can be used for tire inspection, such as the inspection of steel belts and tread integrity.

Further, the systems and methods in accordance with the subject matter described herein can be used for security screening purposes. For example, the systems and methods can be used for screening at airports and seaports. DEI techniques as described herein can be used for screening for plastic and low absorption contrast objects, such as plastic knives, composite guns difficult to detect with conventional X-ray, and plastic explosives. For imaging larger objects, such is for airport baggage inspection, the distance between the X-ray tube and detector can be increased to allow beam divergence. A larger analyzer crystal would be necessary to accommodate a larger fan beam.

The device described provides a mechanism that can be translated into a computed tomography imaging system, or DEI-CT. A DEI-CT system, resembling a third generation conventional computed tomography system, would use the same apparatus but modified for rotation around a central point. Alternatively, the system could remain stationary and the object, sample, or patient could be rotated in the beam. A DEI-CT system of this design would produce images representing X-ray absorption, refraction, and ultra-small angle scatter rejection (extinction), but they would be resolved in three dimensions.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A diffraction enhanced imaging system comprising:
   an X-ray source configured to generate a first X-ray beam;
   a first monochromator crystal positioned to intercept the first X-ray beam for producing a second X-ray beam;
   a second monochromator crystal positioned to intercept the second X-ray beam to produce a third X-ray beam for transmission through an object, wherein the second monochromator crystal has a thickness selected such that a mechanical strain on a side of the first monochromator crystal is the same as a mechanical strain on a side of the second monochromator crystal;
   an analyzer crystal having a thickness selected such that a mechanical strain on a side of the first monochromator crystal is the same as a mechanical strain on a side of the analyzer crystal, wherein the analyzer crystal is positioned to intercept transmitted X-ray beams at angles of incidence of the analyzer crystal; and
   an image detector configured to detect an image of the object from one or more beams diffracted from the analyzer crystal,
   wherein the image detector is configured to:
      detect a first angle image of the object from first diffracted beams emitted from the analyzer crystal positioned at first angular positions; and
      detect a second angle image of the object from second diffracted beams emitted from the analyzer crystal positioned at second angular positions; and
   wherein the system further comprises a computer configured to:
      combine the first and second angle images to derive a refraction and apparent absorption image; and
      derive a mass density image of the object from the refraction image.

2. The system of claim 1 wherein the thicknesses of the analyzer crystal and the second monochromator crystal extend in a first direction, and the first X-ray beam diverges in a second direction substantially perpendicular to the first direction.

3. The system of claim 1 wherein a thickness of the first monochromator crystal is about 0.5 centimeters, the thickness of the second monochromator crystal is about 1 centimeter, and the thickness of the analyzer crystal is about 2 centimeters.

4. The system of claim 1 wherein the thicknesses of the second monochromator crystal and the analyzer crystal are substantially uniform.

5. The system of claim 1 wherein the first and second monochromator crystals are silicon crystals.

6. The system of claim 5 wherein the silicon crystals have [333] reflection.

7. The system of claim 1 wherein the analyzer crystal is a Bragg type crystal.

8. The system of claim 1 wherein the object is a soft tissue object.

9. The system of claim 8 wherein the soft tissue object is breast tissue.

10. The system of claim 1 wherein the third X-ray beam applies a total radiation dosage of less than or equal to about 0.5 mrad to the object.

11. The system of claim 1 wherein the image detector is configured to receive the diffracted beams.

12. The system of claim 1 wherein the image detector is configured to produce a digitized image of the object.

13. The system of claim 1 wherein the image detector is one of a radiographic film and an image plate.

14. The system of claim 1 wherein the image detector is configured to detect the image of the object from the beam diffracted from the analyzer crystal one of at or near a peak of a rocking curve of the analyzer crystal.

15. The system of claim 14 further comprising a computer configured to derive at least one of a diffraction enhanced image, an absorption image, a refraction image, a scatter image, and a mass density image of the object from the detected image.

16. The system of claim 15 wherein the one of at and near the peaks occurs approximately one-half of a Darwin width of the rocking curve.

17. The system of claim 1 wherein the image detector is configured to detect the first angle image of the object from the analyzer crystals at a low rocking curve angle setting of the analyzer crystals, and wherein the image detector is configured to detect the second angle image comprises detecting the second angle image of the object from the analyzer crystals at a high rocking curve angle setting of the analyzer crystals.

18. The system of claim 1 wherein the monochromator crystal is one of germanium and silicon monochromator crystals.

19. The system of claim 1 wherein the monochromator crystal is one of germanium [333] and silicon [333] monochromator crystals.

20. The system of claim 1 comprising a computer configured for adjusting a radiation dose applied by the second X-ray beam to the object.

21. A method for detecting an image of an object, the method comprising:
generating a first X-ray beam;
positioning a first monochromator crystal to intercept the first X-ray beam to produce a second X-ray beam;
positioning a second monochromator crystal to intercept the second X-ray beam to produce a third X-ray beam for transmission through an object, wherein the second monochromator crystal has a thickness selected such that a mechanical strain on a side of the first monochromator crystal is the same as a mechanical strain on a side of the second monochromator crystal;
positioning an analyzer crystal to intercept transmitted X-ray beams at angles of incidence of the analyzer crystal, wherein the analyzer crystal has a thickness selected such that a mechanical strain on a side of the first monochromator crystal is the same as a mechanical strain on a side of the analyzer crystal;
detecting an image of the object from one or more beams diffracted from the analyzer crystal;
detecting a first angle image of the object from first diffracted beams emitted from the analyzer crystal positioned at first angular positions;
detecting a second angle image of the object from second diffracted beams emitted from the analyzer crystal positioned at second angular positions;
combining the first and second angle images to derive a refraction and apparent absorption image; and
deriving a mass density image of the object from the refraction image.

22. The method of claim 21 wherein the thicknesses of the analyzer crystal and the second monochromator crystal extend in a first direction, and the first X-ray beam diverges in a second direction substantially perpendicular to the first direction.

23. The method of claim 21 wherein a thickness of the first monochromator crystal is about 0.5 centimeters, the thickness of the second monochromator crystal is about 1 centimeter, and the thickness of the analyzer crystal is about 2 centimeters.

24. The method of claim 21 wherein the thicknesses of the second monochromator crystal and the analyzer crystal are substantially uniform.

25. The method of claim 21 wherein the first and second monochromator crystals are silicon crystals.

26. The method of claim 25 wherein the silicon crystals have [333] reflection.

27. The method of claim 21 wherein the analyzer crystal is a Bragg type crystal.

28. The method of claim 21 wherein the object is a soft tissue object.

29. The method of claim 28 wherein the soft tissue object is breast tissue.

30. The method of claim 21 wherein the third X-ray beam applies a total radiation dosage of less than or equal to about 0.5 mrad to the object.

31. The method of claim 21 further comprising providing an image detector configured to receive the diffracted beams.

32. The method of claim 21 further comprising providing an image detector configured to produce a digitized image of the object.

33. The method of claim 21 wherein detecting an image of the object comprises providing radiographic film.

34. The method of claim 21 wherein detecting an image of the object comprises providing an image plate.

35. The method of claim 21 further comprising providing an image detector configured to detect the image of the object from the beam diffracted from the analyzer crystal one of at or near a peak of a rocking curve of the analyzer crystal.

36. The method of claim 35 further comprising providing a computer configured to derive at least one of a diffraction enhanced image, an absorption image, a refraction image, a scatter image, and a mass density image of the object from the detected image.

37. The method of claim 36 wherein the one of at and near the peaks occurs approximately one-half of a Darwin width of the rocking curve.

38. The method of claim 21 further comprising:
detecting the first angle image of the object from the analyzer crystals at a low rocking curve angle setting of the analyzer crystals; and
detecting the second angle image comprises detecting the second angle image of the object from the analyzer crystals at a high rocking curve angle setting of the analyzer crystals.

39. The method of claim 21 wherein the monochromator crystal is one of germanium and silicon monochromator crystals.

40. The method of claim 21 wherein the monochromator crystal is one of germanium [333] and silicon [333] monochromator crystals.

41. The method of claim 21 comprising providing a computer configured for adjusting a radiation dose applied by the second X-ray beam to the object.

42. A diffraction enhanced imaging system comprising:
an X-ray source configured to generate first and second X-ray beams;
a plurality of first monochromator crystals being spaced apart substantially along a first direction, and the first monochromator crystals being positioned to intercept the first X-ray beam on surfaces of the first monochromator crystals for producing a third X-ray beam;
a plurality of second monochromator crystals being spaced apart substantially along the first direction, the second monochromator crystals being positioned to intercept the second X-ray beam on surfaces of the second monochromator crystals for producing a fourth X-ray beam, wherein the surfaces of second monochromator crystals at least partially extend in the first direction within the spacings of the first monochromator crystals;
a plurality of third monochromator crystals being spaced apart substantially along the first direction, and the third monochromator crystals being positioned to intercept the third X-ray beam on surfaces of the third monochromator crystals to produce a fifth X-ray beam for transmission through an object;
a plurality of fourth monochromator crystals being spaced apart substantially along the first direction, and the fourth monochromator crystals being positioned to intercept the fourth X-ray beam on surfaces of the fourth monochromator crystals to produce a sixth X-ray beam for transmission through the object, wherein the surfaces of fourth monochromator crystals at least partially extend in the first direction within the spacings of the third monochromator crystals;
a plurality of analyzer crystals positioned to intercept the fifth and sixth X-ray beams at angles of incidence of the analyzer crystals; and
an image detector configured to detect an image of the object from beams diffracted from the analyzer crystals, wherein the image detector is configured to:
detect a first angle image of the object from first diffracted beams emitted from the analyzer crystals positioned at first angular positions; and
detect a second angle image of the object from second diffracted beams emitted from the analyzer crystals positioned at second angular positions; and
wherein the system further comprises a computer configured to:
combine the first and second angle images to derive a refraction and apparent absorption image; and
derive a mass density image of the object from the refraction image.

43. The system of claim 42 wherein the first and second monochromator crystals are spaced from one another along a second direction, wherein the first direction is substantially perpendicular to the second direction.

44. The system of claim 42 wherein the first X-ray beams have a characteristic X-ray energy ranging from about 10 keV to about 70 keV.

45. The system of claim 42 wherein each of the monochromator crystals are matched in orientation and lattice planes to a respective one of the analyzer crystals.

46. The system of claim 42 wherein the monochromator crystals are symmetric crystals.

47. The system of claim 46 wherein the monochromator crystals are silicon crystals.

48. The system of claim 47 wherein the silicon crystals have [333] reflection.

49. The system of claim 42 wherein the analyzer crystals are Bragg type crystals.

50. The system of claim 42 wherein the object is a soft tissue object.

51. The system of claim 50 wherein the soft tissue object is breast tissue.

52. The system of claim 42 wherein the fifth and sixth X-ray beams apply a total radiation dosage of less than or equal to about 0.5 mrad to the object.

53. The system of claim 42 wherein the image detector is configured to receive the diffracted beams.

54. The system of claim 53 wherein the image detector is configured to produce a digitized image of the object.

55. The system of claim 42 wherein the image detector is one of a radiographic film and an image plate.

56. The system of claim 42 wherein the image detector is configured to detect the image of the object from the beam diffracted from the analyzer crystals one of at or near a peak of a rocking curve of the analyzer crystals.

57. The system of claim 56 further comprising a computer configured to derive at least one of a diffraction enhanced image, an absorption image, a refraction image, a scatter image, and a mass density image of the object from the detected image.

58. The system of claim 56 wherein the one of at and near the peaks occurs approximately one-half of a Darwin width of the rocking curve.

59. The system of claim 42 wherein the image detector is configured to detect the first angle image of the object from the analyzer crystals at a low rocking curve angle setting of the analyzer crystals, and wherein the image detector is configured to detect the second angle image comprises detecting the second angle image of the object from the analyzer crystals at a high rocking curve angle setting of the analyzer crystals.

60. The system of claim 42 wherein the monochromator crystals are one of germanium and silicon monochromator crystals.

61. The system of claim 42 wherein the monochromator crystals are one of germanium [333] and silicon [333] monochromator crystals.

62. The system of claim 42 further comprising a computer configured for adjusting a radiation dose applied by the fifth and sixth X-ray beams to the object.

63. A method for detecting an image of an object, the method comprising:
generating first and second X-ray beams;
providing a plurality of first monochromator crystals being spaced apart substantially along a first direction;
positioning the first monochromator crystals to intercept the first X-ray beam on surfaces of the first monochromator crystals for producing a third X-ray beam;
providing a plurality of second monochromator crystals being spaced apart substantially along the first direction;
positioning the second monochromator crystals to intercept the second X-ray beam on surfaces of the second monochromator crystals for producing a fourth X-ray beam, wherein the surfaces of second monochromator crystals at least partially extend in the first direction within the spacings of the first monochromator crystals;
providing a plurality of third monochromator crystals being spaced apart substantially along the first direction;

positioning the third monochromator crystals to intercept the third X-ray beam on surfaces of the third monochromator crystals to produce a fifth X-ray beam for transmission through an object;

providing a plurality of fourth monochromator crystals being spaced apart substantially along the first direction;

positioning the fourth monochromator crystals to intercept the fourth X-ray beam on surfaces of the fourth monochromator crystals to produce a sixth X-ray beam for transmission through the object, wherein the surfaces of fourth monochromator crystals at least partially extend in the first direction within the spacings of the third monochromator crystals;

providing a plurality of analyzer crystals positioned to intercept the fifth and sixth X-ray beams at angles of incidence of the analyzer crystals;

detecting an image of the object from beams diffracted from the analyzer crystals;

detecting a first angle image of the object from first diffracted beams emitted from the analyzer crystals positioned at first angular positions;

detecting a second angle image of the object from second diffracted beams emitted from the analyzer crystals positioned at second angular positions;

combining the first and second angle images to derive a refraction and apparent absorption image; and deriving a mass density image of the object from the refraction image.

64. The method of claim 63 wherein the first and second monochromator crystals are spaced from one another along a second direction, wherein the first direction is substantially perpendicular to the second direction.

65. The method of claim 63 wherein the first X-ray beams have a characteristic X-ray energy ranging from about 10 keV to about 70 keV.

66. The method of claim 63 wherein each of the monochromator crystals are matched in orientation and lattice planes to a respective one of the analyzer crystals.

67. The method of claim 63 wherein the monochromator crystals are symmetric crystals.

68. The method of claim 63 wherein the monochromator crystals are silicon crystals.

69. The method of claim 68 wherein the silicon crystals have [333] reflection.

70. The method of claim 63 wherein the analyzer crystals are Bragg type crystals.

71. The method of claim 63 wherein the object is a soft tissue object.

72. The method of claim 71 wherein the soft tissue object is breast tissue.

73. The method of claim 63 wherein the fifth and sixth X-ray beams apply a total radiation dosage of less than or equal to about 0.5 mrad to the object.

74. The method of claim 63 further comprising providing an image detector configured to receive the diffracted beams.

75. The method of claim 74 wherein the image detector is configured to produce a digitized image of the object.

76. The method of claim 74 wherein the image detector is one of a radiographic film and an image plate.

77. The method of claim 74 wherein the image detector is configured to detect the image of the object from the beam diffracted from the analyzer crystals one of at or near a peak of a rocking curve of the analyzer crystals.

78. The method of claim 77 further comprising providing a computer configured to derive at least one of a diffraction enhanced image, an absorption image, a refraction image, a scatter image, and a mass density image of the object from the detected image.

79. The method of claim 77 wherein the one of at and near the peaks occurs approximately one-half of a Darwin width of the rocking curve.

80. The method of claim 63 further comprising:
detecting the first angle image of the object from the analyzer crystals at a low rocking curve angle setting of the analyzer crystals; and
detecting the second angle image of the object from the analyzer crystals at a high rocking curve angle setting of the analyzer crystals.

81. The method of claim 63 wherein the monochromator crystals are one of germanium and silicon monochromator crystals.

82. The method of claim 63 wherein the monochromator crystals are one of germanium [333] and silicon [333] monochromator crystals.

83. The method of claim 63 further comprising a computer configured for adjusting a radiation dose applied by the fifth and sixth X-ray beams to the object.

84. A diffraction enhanced imaging system comprising:
an X-ray source configured to generate at least first and second X-ray beams;
a plurality of first monochromator crystals being spaced apart substantially along a first direction, and the first monochromator crystals being positioned to intercept the first X-ray beam on surfaces of the first monochromator crystals for producing a third X-ray beam;
a plurality of second monochromator crystals being spaced apart substantially along the first direction, the second monochromator crystals being positioned to intercept the second X-ray beam on surfaces of the second monochromator crystals for producing a fourth X-ray beam, wherein the surfaces of second monochromator crystals at least partially extend in the first direction within the spacings of the first monochromator crystals;
a plurality of third monochromator crystals being spaced apart substantially along the first direction, and the third monochromator crystals being positioned to intercept the third X-ray beam on surfaces of the third monochromator crystals to produce a fifth X-ray beam for transmission through an object;
a plurality of fourth monochromator crystals being spaced apart substantially along the first direction, and the fourth monochromator crystals being positioned to intercept the fourth X-ray beam on surfaces of the fourth monochromator crystals to produce a sixth X-ray beam for transmission through an object, wherein the surfaces of fourth monochromator crystals at least partially extend in the first direction within the spacings of the third monochromator crystals;
a plurality of first analyzer crystals being spaced apart substantially along the first direction, and the first analyzer crystals being positioned to intercept the fifth X-ray beams at angles of incidence of the first analyzer crystals;
a plurality of second analyzer crystals being spaced apart substantially along the first direction, the second analyzer crystals being positioned to intercept the sixth X-ray beams at angles of incidence of the second analyzer crystals, and the surfaces of fourth monochromator crystals at least partially extend in the first direction within the spacings of the third monochromator crystals;

an image detector configured to detect an image of the object from beams diffracted from the first and second analyzer crystals, wherein the image detector is configured to:
- detect a first angle image of the object from first diffracted beams emitted from the analyzer crystals positioned at first angular positions; and
- detect a second angle image of the object from second diffracted beams emitted from the analyzer crystals positioned at second angular positions; and wherein the system further comprises a computer configured to:
- combine the first and second angle images to derive a refraction and apparent absorption image; and
- derive a mass density image of the object from the refraction image.

85. The system of claim 84 wherein the first and second monochromator crystals are spaced from one another along a second direction, wherein the first direction is substantially perpendicular to the second direction.

86. The system of claim 84 wherein the first and second monochromator crystals are spaced from one another along a second direction, wherein the first direction is substantially perpendicular to the second direction.

87. The system of claim 84 wherein the first X-ray beams have a characteristic X-ray energy ranging from about 10 keV to about 70 keV.

88. The system of claim 84 wherein each of the monochromator crystals are matched in orientation and lattice planes to a respective one of the analyzer crystals.

89. The system of claim 84 wherein the monochromator crystals are symmetric crystals.

90. The system of claim 84 wherein the monochromator crystals are silicon crystals.

91. The system of claim 90 wherein the silicon crystals have [333] reflection.

92. The system of claim 90 wherein the analyzer crystals are Bragg type crystals.

93. The system of claim 90 wherein the object is a soft tissue object.

94. The system of claim 93 wherein the soft tissue object is breast tissue.

95. The system of claim 90 wherein the fifth and sixth X-ray beams apply a total radiation dosage of less than or equal to about 0.5 mrad to the object.

96. The system of claim 84 wherein the image detector is configured to receive the diffracted beams.

97. The system of claim 96 wherein the image detector is configured to produce a digitized image of the object.

98. The system of claim 84 wherein the image detector is one of a radiographic film and an image plate.

99. The system of claim 84 wherein the image detector is configured to detect the image of the object from the beam diffracted from the analyzer crystals one of at or near a peak of a rocking curve of the analyzer crystals.

100. The system of claim 99 further comprising a computer configured to derive at least one of a diffraction enhanced image, an absorption image, a refraction image, a scatter image, and a mass density image of the object from the detected image.

101. The system of claim 99 wherein the one of at and near the peaks occurs approximately one-half of a Darwin width of the rocking curve.

102. The system of claim 84 wherein the image detector is configured to detect the first angle image of the object from the analyzer crystals at a low rocking curve angle setting of the analyzer crystals, and wherein the image detector is configured to detect the second angle image comprises detecting the second angle image of the object from the analyzer crystals at a high rocking curve angle setting of the analyzer crystals.

103. The system of claim 84 wherein the monochromator crystals are one of germanium and silicon monochromator crystals.

104. The system of claim 84 wherein the monochromator crystals are one of germanium [333] and silicon [333] monochromator crystals.

105. The system of claim 84 comprising a computer configured for adjusting a radiation dose applied by the third X-ray beams to the object.

* * * * *